US012731206B2

(12) United States Patent
Keller et al.

(10) Patent No.: US 12,731,206 B2
(45) Date of Patent: Sep. 8, 2026

(54) SYSTEM AND METHOD OF PROVIDING REAL-TIME DYNAMIC IMAGERY OF A MEDICAL PROCEDURE SITE USING MULTIPLE MODALITIES

(71) Applicant: INNEROPTIC TECHNOLOGY, INC., Hillsborough, NC (US)

(72) Inventors: Kurtis P. Keller, Hillsborough, NC (US); Sharif A. Razzaque, Boulder, CO (US); Andrei State, Chapel Hill, NC (US); Caroline K. Green, Chapel Hill, NC (US); Jeremy D. Ackerman, Port Jefferson Station, NY (US)

(73) Assignee: INNEROPTIC TECHNOLOGY, INC., Hillsborough, NC (US)

(*) Notice: Subject to any disclaimer, the term of this patent is extended or adjusted under 35 U.S.C. 154(b) by 12 days.

(21) Appl. No.: 18/048,711

(22) Filed: Oct. 21, 2022

(65) Prior Publication Data

US 2023/0222624 A1 Jul. 13, 2023

Related U.S. Application Data

(63) Continuation of application No. 16/920,560, filed on Jul. 3, 2020, now Pat. No. 11,481,868, which is a (Continued)

(51) Int. Cl.

*G06T 3/16* (2024.01)
*A61B 1/00* (2006.01)

(Continued)

(52) U.S. Cl.

CPC .............. *G06T 3/16* (2024.01); *A61B 1/0005* (2013.01); *A61B 1/042* (2013.01); *A61B 8/12* (2013.01);

(Continued)

(58) Field of Classification Search

None

See application file for complete search history.

(56) References Cited

U.S. PATENT DOCUMENTS 3,556,079 A 1/1971 Omizo
4,058,114 A 11/1977 Soldner (Continued)

FOREIGN PATENT DOCUMENTS

EP 0 427 358 5/1991
JP S63-290550 A 11/1988

(Continued)

OTHER PUBLICATIONS

U.S. Appl. No. 11/828,826 including without limitation Office Actions, Amendments, Remarks, and any other potentially relevant documents, filed Jul. 26, 2007, Keller et al.

(Continued)

*Primary Examiner* — Christopher Braniff

(74) *Attorney, Agent, or Firm* — Knobbe, Martens, Olson & Bear, LLP

(57) ABSTRACT

A system and method of providing composite real-time dynamic imagery of a medical procedure site from multiple modalities which continuously and immediately depicts the current state and condition of the medical procedure site synchronously with respect to each modality and without undue latency is disclosed. The composite real-time dynamic imagery may be provided by spatially registering multiple real-time dynamic video streams from the multiple modalities to each other. Spatially registering the multiple real-time dynamic video streams to each other may provide a continuous and immediate depiction of the medical procedure site with an unobstructed and detailed view of a region of interest at the medical procedure site at multiple depths. A user may thereby view a single, accurate, and current composite real-time dynamic imagery of a region of (Continued)

interest at the medical procedure site as the user performs a medical procedure.

9 Claims, 8 Drawing Sheets

Related U.S. Application Data continuation of application No. 16/177,894, filed on Nov. 1, 2018, now Pat. No. 10,733,700, which is a continuation of application No. 15/598,616, filed on May 18, 2017, now Pat. No. 10,127,629, which is a continuation of application No. 13/936,951, filed on Jul. 8, 2013, now Pat. No. 9,659,345, which is a continuation of application No. 12/760,274, filed on Apr. 14, 2010, now Pat. No. 8,482,606, which is a continuation of application No. 11/833,134, filed on Aug. 2, 2007, now Pat. No. 7,728,868.

(60) Provisional application No. 60/856,670, filed on Nov. 6, 2006, provisional application No. 60/834,932, filed on Aug. 2, 2006.

(51) Int. Cl.

| | |
|---|---|
| ***A61B 1/04*** | (2006.01) |
| ***A61B 1/313*** | (2006.01) |
| ***A61B 8/00*** | (2006.01) |
| ***A61B 8/12*** | (2006.01) |
| ***H04N 7/18*** | (2006.01) |

(52) U.S. Cl.

CPC ............ *A61B 8/463* (2013.01); *A61B 8/5238* (2013.01); *H04N 7/181* (2013.01); *A61B 1/313* (2013.01)

(56) References Cited

U.S. PATENT DOCUMENTS

| | | | |
|---|---|---|---|
| RE30,397 | E | 9/1980 | King |
| 4,249,539 | A | 2/1981 | Vilkomerson et al. |
| 4,294,544 | A | 10/1981 | Altschuler et al. |
| 4,390,025 | A | 6/1983 | Takemura et al. |
| 4,407,294 | A | 10/1983 | Vilkomerso |
| 4,431,006 | A | 2/1984 | Trimmer et al. |
| 4,567,896 | A | 2/1986 | Barnea et al. |
| 4,583,538 | A | 4/1986 | Onik et al. |
| 4,620,546 | A | 11/1986 | Aida et al. |
| 4,671,292 | A | 6/1987 | Matzuk |
| 4,839,836 | A | 6/1989 | Fonsalas |
| 4,862,873 | A | 9/1989 | Yajima et al. |
| 4,884,219 | A | 11/1989 | Waldren |
| 4,899,756 | A | 2/1990 | Sonek |
| 4,911,173 | A | 3/1990 | Terwillige |
| 4,945,305 | A | 7/1990 | Blood |
| 5,076,279 | A | 12/1991 | Arenson et al. |
| 5,078,140 | A | 1/1992 | Kwoh |
| 5,078,142 | A | 1/1992 | Siczek et al. |
| 5,095,910 | A | 3/1992 | Powers |
| 5,109,276 | A | 4/1992 | Nudelman et al. |
| 5,156,144 | A | 10/1992 | Iwasaki et al. |
| 5,158,088 | A | 10/1992 | Nelson et al. |
| 5,161,536 | A | 11/1992 | Vikomerson et al. |
| 5,193,120 | A | 3/1993 | Gamache et al. |
| 5,209,235 | A | 5/1993 | Brisken et al. |
| 5,249,581 | A | 10/1993 | Horbal et al. |
| 5,251,127 | A | 10/1993 | Raab |
| 5,261,404 | A | 11/1993 | Mick et al. |
| 5,265,610 | A | 11/1993 | Darrow et al. |
| 5,271,400 | A | 12/1993 | Dumoulin et al. |
| 5,307,153 | A | 4/1994 | Maruyama et al. |
| 5,309,913 | A | 5/1994 | Kormos et al. |
| 5,323,002 | A | 6/1994 | Sampsell et al. |
| 5,371,543 | A | 12/1994 | Anderson |
| 5,383,454 | A | 1/1995 | Bucholz |
| 5,394,875 | A | 3/1995 | Lewis et al. |
| 5,411,026 | A | 5/1995 | Carol |
| 5,433,198 | A | 7/1995 | Desai |
| 5,433,739 | A | 7/1995 | Sluijter |
| 5,443,489 | A | 8/1995 | Ben-Haim |
| 5,446,798 | A | 8/1995 | Morita et al. |
| 5,447,154 | A | 9/1995 | Cinquin et al. |
| 5,452,024 | A | 9/1995 | Sampsell |
| 5,457,493 | A | 10/1995 | Leddy et al. |
| 5,474,073 | A | 12/1995 | Schwartz et al. |
| 5,476,096 | A | 12/1995 | Olstad et al. |
| 5,483,961 | A | 1/1996 | Kelly et al. |
| 5,488,431 | A | 1/1996 | Gove et al. |
| 5,489,952 | A | 2/1996 | Gove et al. |
| 5,491,510 | A | 2/1996 | Gove |
| 5,494,039 | A | 2/1996 | Onik et al. |
| 5,503,152 | A | 4/1996 | Oakley et al. |
| 5,505,204 | A | 4/1996 | Picot et al. |
| 5,515,856 | A | 5/1996 | Olstad et al. |
| 5,517,990 | A | 5/1996 | Kalfas et al. |
| 5,526,051 | A | 6/1996 | Gove et al. |
| 5,526,812 | A | 6/1996 | Dumoulin et al. |
| 5,529,070 | A | 6/1996 | Augustine et al. |
| 5,531,227 | A | 7/1996 | Schneider |
| 5,532,997 | A | 7/1996 | Pauli |
| 5,541,723 | A | 7/1996 | Tanaka |
| 5,558,091 | A | 9/1996 | Acker et al. |
| 5,568,811 | A | 10/1996 | Olstad |
| 5,570,135 | A | 10/1996 | Gove et al. |
| 5,579,026 | A | 11/1996 | Tabata |
| 5,581,271 | A | 12/1996 | Kraemer |
| 5,588,948 | A | 12/1996 | Takahashi et al. |
| 5,608,468 | A | 3/1997 | Gove et al. |
| 5,608,849 | A | 3/1997 | King, Jr. |
| 5,611,345 | A | 3/1997 | Hibbeln |
| 5,611,353 | A | 3/1997 | Dance et al. |
| 5,612,753 | A | 3/1997 | Poradish et al. |
| 5,625,408 | A | 4/1997 | Matsugu et al. |
| 5,628,327 | A | 5/1997 | Unger et al. |
| 5,629,794 | A | 5/1997 | Magel et al. |
| 5,630,027 | A | 5/1997 | Venkateswar et al. |
| 5,647,361 | A | 7/1997 | Damadian |
| 5,647,373 | A | 7/1997 | Paltieli et al. |
| 5,660,185 | A | 8/1997 | Shmulewitz et al. |
| 5,662,111 | A | 9/1997 | Cosman |
| 5,699,444 | A | 12/1997 | Palm |
| 5,701,898 | A | 12/1997 | Adam et al. |
| 5,701,900 | A | 12/1997 | Shehada et al. |
| 5,726,670 | A | 3/1998 | Tabata et al. |
| 5,728,044 | A | 3/1998 | Shan |
| 5,758,650 | A | 6/1998 | Miller et al. |
| 5,766,135 | A | 6/1998 | Terwilliger |
| 5,784,098 | A | 7/1998 | Shoji et al. |
| 5,792,147 | A | 8/1998 | Evans et al. |
| 5,793,701 | A | 8/1998 | Wright et al. |
| 5,797,849 | A | 8/1998 | Vesely et al. |
| 5,806,521 | A | 9/1998 | Morimoto et al. |
| 5,807,395 | A | 9/1998 | Mulier et al. |
| 5,810,008 | A | 9/1998 | Dekel et al. |
| 5,817,022 | A | 10/1998 | Vesely |
| 5,820,554 | A | 10/1998 | Davis et al. |
| 5,820,561 | A | 10/1998 | Olstad et al. |
| 5,829,439 | A | 11/1998 | Yokosawa et al. |
| 5,829,444 | A | 11/1998 | Ferre et al. |
| 5,851,183 | A | 12/1998 | Bodiolz |
| 5,870,136 | A | 2/1999 | Fuchs et al. |
| 5,891,034 | A | 4/1999 | Bucholz |
| 5,920,395 | A | 7/1999 | Schulz |
| 5,961,527 | A | 10/1999 | Whitmore, III et al. |
| 5,967,980 | A | 10/1999 | Ferre et al. |
| 5,967,991 | A | 10/1999 | Gardineer et al. |
| 5,991,085 | A | 11/1999 | Rallison et al. |
| 6,016,439 | A | 1/2000 | Acker |
| 6,019,724 | A | 2/2000 | Gronningsaeter et al. |
| 6,048,312 | A | 4/2000 | Ishrak et al. |
| 6,064,749 | A | 5/2000 | Hirota et al. |
| 6,091,546 | A | 7/2000 | Spitzer |

(56) References Cited

U.S. PATENT DOCUMENTS 6,095,982 A 8/2000 Richards-Kortum et al.
6,099,471 A 8/2000 Torp et al.
6,108,130 A 8/2000 Raj
6,122,538 A 9/2000 Sliwa, Jr. et al.
6,122,541 A 9/2000 Cosman et al.
6,160,666 A 12/2000 Rallison et al.
6,167,296 A 12/2000 Shahidi
6,181,371 B1 1/2001 Maguire, Jr.
RE37,088 E 3/2001 Olstad et al.
6,216,029 B1 4/2001 Paltieli
6,241,725 B1 6/2001 Cosman
6,245,017 B1 6/2001 Hashimoto et al.
6,246,784 B1 6/2001 Summers et al.
6,246,898 B1 6/2001 Vesely et al.
6,248,101 B1 6/2001 Witmore, III et al.
6,261,234 B1 7/2001 Lin
6,341,016 B1 1/2002 Malione
6,348,058 B1 2/2002 Melken et al.
6,350,238 B1 2/2002 Olstad et al.
6,352,507 B1 3/2002 Torp et al.
6,379,302 B1 4/2002 Kessman et al.
6,385,475 B1 5/2002 Cinquin et al.
6,442,417 B1 8/2002 Shahidi et al.
6,447,450 B1 9/2002 Olstad
6,456,868 B2 9/2002 Saito et al.
6,470,207 B1 10/2002 Simon et al.
6,471,366 B1 10/2002 Hughson et al.
6,477,400 B1 11/2002 Barrick
6,478,793 B1 11/2002 Cosman et al.
6,503,195 B1 1/2003 Keller et al.
6,511,418 B2 1/2003 Shahidi et al.
6,517,485 B2 2/2003 Torp et al.
6,518,939 B1 2/2003 Kikuchi
6,527,443 B1 3/2003 Vilsmeier
6,529,758 B2 3/2003 Shahidi
6,537,217 B1 3/2003 Bjaerum et al.
6,545,706 B1 4/2003 Edwards et al.
6,546,279 B1 4/2003 Bova et al.
6,547,777 B2 4/2003 Di Resta et al.
6,551,325 B2 4/2003 Neubauer et al.
6,570,566 B1 5/2003 Yoshigahara
6,575,969 B1 6/2003 Rittman, III et al.
6,579,240 B2 6/2003 Bjaerum et al.
6,587,711 B1 7/2003 Alfano et al.
6,591,130 B2 7/2003 Shahidi
6,592,522 B2 7/2003 Bjaerum et al.
6,594,517 B1 7/2003 Nevo
6,597,818 B2 7/2003 Kumar et al.
6,604,404 B2 8/2003 Paltieli et al.
6,616,610 B2 9/2003 Steininger et al.
6,626,832 B1 9/2003 Paltieli et al.
6,652,462 B2 11/2003 Bjaerum et al.
6,669,635 B2 12/2003 Kessman et al.
6,676,599 B2 1/2004 Torp et al.
6,689,067 B2 2/2004 Sauer et al.
6,695,786 B2 2/2004 Wang et al.
6,711,429 B1 3/2004 Gilboa et al.
6,725,082 B2 4/2004 Sati et al.
6,733,458 B1 5/2004 Steins et al.
6,764,449 B2 7/2004 Lee et al.
6,766,184 B2 7/2004 Utzinger et al.
6,768,496 B2 7/2004 Bieger et al.
6,775,404 B1 8/2004 Pagoulatos et al.
6,782,287 B2 8/2004 Grzeszczuk et al.
6,783,524 B2 8/2004 Anderson et al.
6,827,723 B2 12/2004 Carson
6,863,655 B2 3/2005 Bjaerum et al.
6,873,867 B2 3/2005 Vilsmeier
6,875,179 B2 4/2005 Ferguson et al.
6,881,214 B2 4/2005 Cosman et al.
6,895,268 B1 5/2005 Rahn et al.
6,915,150 B2 7/2005 Cinquin et al.
6,917,827 B2 7/2005 Kienzle, III
6,923,817 B2 8/2005 Carson et al.
6,936,048 B2 8/2005 Hurst
6,947,783 B2 9/2005 Immerz
6,968,224 B2 11/2005 Kessman et al.
6,978,167 B2 12/2005 Dekel et al.
7,008,373 B2 3/2006 Stoianovici et al.
7,033,360 B2 4/2006 Cinquin et al.
7,072,707 B2 7/2006 Galloway, Jr. et al.
7,077,807 B2 7/2006 Torp et al.
7,093,012 B2 8/2006 Oltad et al.
7,110,013 B2 9/2006 Ebersole et al.
7,171,255 B2 1/2007 Holupka et al.
7,209,776 B2 4/2007 Leitner
7,245,746 B2 7/2007 Bjaerum et al.
7,248,232 B1 7/2007 Yamazaki et al.
7,261,694 B2 8/2007 Torp et al.
7,313,430 B2 12/2007 Urquhart et al.
7,331,932 B2 2/2008 Leitner
7,351,205 B2 4/2008 Szczech et al.
7,379,769 B2 5/2008 Piron et al.
7,385,708 B2 6/2008 Ackerman et al.
7,392,076 B2 6/2008 Moctezuma de La Barrera
7,398,116 B2 7/2008 Edwards
7,466,303 B2 12/2008 Yi et al.
7,480,533 B2 1/2009 Cosman et al.
7,505,809 B2 3/2009 Strommer et al.
7,588,541 B2 9/2009 Floyd et al.
7,596,267 B2 9/2009 Accomazzi et al.
7,652,259 B2 1/2010 Kimchy et al.
7,662,128 B2 2/2010 Salcudean et al.
7,678,052 B2 3/2010 Torp et al.
7,728,868 B2 6/2010 Razzaque et al.
7,747,305 B2 6/2010 Dean et al.
7,797,032 B2 9/2010 Martinelli et al.
7,798,965 B2 9/2010 Torp et al.
7,833,168 B2 11/2010 Taylor et al.
7,833,221 B2 11/2010 Voegele et al.
7,846,103 B2 12/2010 Cannon, Jr. et al.
7,876,942 B2 1/2011 Gilboa
7,889,905 B2 2/2011 Higgins et al.
7,912,849 B2 3/2011 Ohrn et al.
7,920,909 B2 4/2011 Lyon et al.
7,962,193 B2 6/2011 Edwards et al.
7,976,469 B2 7/2011 Bonde et al.
8,023,712 B2 9/2011 Ikuma et al.
8,038,631 B1 10/2011 Sanghvi et al.
8,041,413 B2 10/2011 Barbagli et al.
8,050,736 B2 11/2011 Piron et al.
8,052,636 B2 11/2011 Moll et al.
8,066,644 B2 11/2011 Sarkar et al.
8,073,528 B2 12/2011 Zhao et al.
8,086,298 B2 12/2011 Whitmore, III et al.
8,135,669 B2 3/2012 Olstad et al.
8,137,281 B2 3/2012 Huang et al.
8,147,408 B2 4/2012 Bunce et al.
8,152,724 B2 4/2012 Ridley et al.
8,167,805 B2 5/2012 Emery et al.
8,216,149 B2 7/2012 Oonuki et al.
8,221,322 B2 7/2012 Wang et al.
8,228,028 B2 7/2012 Schneider
8,257,264 B2 9/2012 Park et al.
8,296,797 B2 10/2012 Olstad et al.
8,340,379 B2 12/2012 Razzaque et al.
8,350,902 B2 1/2013 Razzaque et al.
8,482,606 B2 7/2013 Razzaque et al.
8,554,307 B2 10/2013 Razzaque et al.
8,585,598 B2 11/2013 Razzaque et al.
8,641,621 B2 2/2014 Razzaque et al.
8,670,816 B2 3/2014 Green et al.
8,690,776 B2 4/2014 Razzaque et al.
8,831,310 B2 9/2014 Razzaque et al.
8,977,339 B1 3/2015 Wu et al.
9,107,698 B2 8/2015 Razzaque et al.
9,265,572 B2 2/2016 Fuchs et al.
9,282,947 B2 3/2016 Razzaque et al.
9,364,294 B2 6/2016 Razzaque et al.
9,398,936 B2 7/2016 Razzaque et al.
9,659,345 B2 5/2017 Razzaque et al.
9,675,319 B1 6/2017 Razzaque et al.
9,901,406 B2 2/2018 State et al.
9,949,700 B2 4/2018 Razzaque et al.

(56) References Cited

U.S. PATENT DOCUMENTS 10,026,191 B2 7/2018 Accomando et al.
10,127,629 B2 11/2018 Razzaque et al.
10,136,951 B2 11/2018 Razzaque et al.
10,188,467 B2 1/2019 Razzaque et al.
10,278,778 B2 5/2019 State et al.
10,314,559 B2 6/2019 Razzaque et al.
10,398,513 B2 9/2019 Razzaque et al.
10,433,814 B2 10/2019 Razzaque et al.
10,733,700 B2 8/2020 Keller et al.
10,772,686 B2 9/2020 State et al.
10,820,944 B2 11/2020 State et al.
10,820,946 B2 11/2020 Heaney et al.
11,103,200 B2 8/2021 Kohli et al.
11,179,136 B2 11/2021 Kohli et al.
11,259,879 B2 3/2022 Kohli et al.
11,369,439 B2 6/2022 State et al.
11,464,575 B2 10/2022 Heaney et al.
11,464,578 B2 10/2022 State et al.
11,481,868 B2 10/2022 Keller et al.
11,484,365 B2 11/2022 Kohli et al.
11,534,245 B2 12/2022 Heaney et al.
11,684,429 B2 6/2023 State et al.
11,931,117 B2 3/2024 Heaney et al.
2001/0007919 A1 7/2001 Shahidi
2001/0016804 A1 8/2001 Cunningham et al.
2001/0031920 A1 10/2001 Kaufman et al.
2001/0041838 A1 11/2001 Holupka et al.
2001/0045979 A1 11/2001 Matsumoto et al.
2002/0010384 A1 1/2002 Shahidi et al.
2002/0032772 A1 3/2002 Olstad et al.
2002/0049375 A1 4/2002 Strommer et al.
2002/0077540 A1 6/2002 Kienzle, III
2002/0077543 A1 6/2002 Grzeszczuk et al.
2002/0103431 A1 8/2002 Toker et al.
2002/0105484 A1 8/2002 Navab et al.
2002/0135673 A1 9/2002 Favalora et al.
2002/0138008 A1 9/2002 Tsujita et al.
2002/0140814 A1 10/2002 Cohen-Solal et al.
2002/0156375 A1 10/2002 Kessmam et al.
2002/0198451 A1 12/2002 Carson
2003/0032878 A1 2/2003 Shahidi
2003/0040743 A1 2/2003 Cosman et al.
2003/0056799 A1 3/2003 Young et al.
2003/0073901 A1 4/2003 Simon et al.
2003/0090682 A1* 5/2003 Gooch ................ G01B 11/002 356/620
2003/0135119 A1 7/2003 Lee et al.
2003/0163142 A1 8/2003 Paltieli et al.
2003/0164172 A1 9/2003 Chumas et al.
2003/0231789 A1 12/2003 Willis et al.
2003/0233123 A1 12/2003 Kindlein et al.
2004/0034313 A1 2/2004 Leitner
2004/0078036 A1 4/2004 Keidar
2004/0095507 A1 5/2004 Bishop et al.
2004/0116810 A1 6/2004 Olstad
2004/0147920 A1 7/2004 Keidar
2004/0152970 A1 8/2004 Hunter et al.
2004/0181144 A1 9/2004 Cinquin et al.
2004/0215071 A1 10/2004 Frank et al.
2004/0238732 A1 12/2004 State et al.
2004/0243146 A1 12/2004 Chesbrough et al.
2004/0243148 A1 12/2004 Wasielewski
2004/0249281 A1 12/2004 Olstad
2004/0249282 A1 12/2004 Olstad
2004/0254454 A1 12/2004 Kockro
2005/0010098 A1 1/2005 Frigstad et al.
2005/0033160 A1 2/2005 Yamagata et al.
2005/0085717 A1 4/2005 Shahidi
2005/0085718 A1 4/2005 Shahidi
2005/0090733 A1 4/2005 Van Der Lugt et al.
2005/0090742 A1 4/2005 Mine et al.
2005/0107679 A1 5/2005 Geiger et al.
2005/0111733 A1 5/2005 Fors et al.
2005/0159641 A1 7/2005 Kanai
2005/0182316 A1 8/2005 Burdette et al.
2005/0192564 A1 9/2005 Cosman et al.
2005/0219552 A1 10/2005 Ackerman et al.
2005/0222574 A1 10/2005 Giordano et al.
2005/0231532 A1 10/2005 Suzuki et al.
2005/0240094 A1 10/2005 Pichon et al.
2005/0251148 A1 11/2005 Friedrich
2006/0004275 A1 1/2006 Vija et al.
2006/0020204 A1 1/2006 Serra et al.
2006/0036162 A1 2/2006 Shahidi et al.
2006/0052792 A1 3/2006 Boettiger et al.
2006/0058609 A1 3/2006 Olstad
2006/0058610 A1 3/2006 Olstad
2006/0058674 A1 3/2006 Olstad
2006/0058675 A1 3/2006 Olstad
2006/0100505 A1 5/2006 Viswanathan
2006/0122495 A1 6/2006 Kienzle
2006/0135866 A1 6/2006 Namii et al.
2006/0184040 A1 8/2006 Keller et al.
2006/0193504 A1 8/2006 Salgo et al.
2006/0229594 A1 10/2006 Francischelli et al.
2006/0235290 A1 10/2006 Gabriel et al.
2006/0235538 A1 10/2006 Rochetin et al.
2006/0241450 A1 10/2006 Da Silva et al.
2006/0253030 A1 11/2006 Altmann et al.
2006/0253032 A1 11/2006 Altmann et al.
2006/0271056 A1 11/2006 Terrill-Grisoni et al.
2006/0282023 A1 12/2006 Leitner
2006/0293643 A1 12/2006 Wallace et al.
2007/0002582 A1 1/2007 Burwell et al.
2007/0016035 A1 1/2007 Hashimoto
2007/0024617 A1 2/2007 Poole
2007/0032906 A1 2/2007 Sutherland et al.
2007/0073155 A1 3/2007 Park et al.
2007/0073455 A1 3/2007 Oyobe et al.
2007/0078346 A1 4/2007 Park et al.
2007/0167699 A1 7/2007 Lathuiliere et al.
2007/0167701 A1 7/2007 Sherman
2007/0167705 A1 7/2007 Chiang et al.
2007/0167771 A1 7/2007 Olstad
2007/0167801 A1 7/2007 Webler et al.
2007/0225553 A1* 9/2007 Shahidi ................. A61B 90/36 600/103
2007/0239281 A1 10/2007 Gotte et al.
2007/0244488 A1 10/2007 Metzger et al.
2007/0255136 A1 11/2007 Kristofferson et al.
2007/0270718 A1 11/2007 Rochetin et al.
2007/0276234 A1 11/2007 Shahidi
2007/0291000 A1 12/2007 Liang et al.
2008/0004481 A1 1/2008 Bax et al.
2008/0004516 A1 1/2008 DiSilvestro et al.
2008/0007720 A1 1/2008 Mittal
2008/0039723 A1 2/2008 Suri et al.
2008/0051910 A1 2/2008 Kammerzell et al.
2008/0091106 A1 4/2008 Kim et al.
2008/0114235 A1 5/2008 Unal et al.
2008/0146939 A1 6/2008 McMorrow et al.
2008/0161824 A1 7/2008 McMillen
2008/0183080 A1 7/2008 Abraham
2008/0200794 A1 8/2008 Teichman et al.
2008/0208031 A1 8/2008 Kurpad et al.
2008/0208081 A1 8/2008 Murphy et al.
2008/0214932 A1 9/2008 Mollard et al.
2008/0232679 A1 9/2008 Hahn et al.
2008/0287794 A1 11/2008 Li et al.
2008/0287805 A1 11/2008 Li
2008/0287837 A1 11/2008 Makin et al.
2009/0024030 A1 1/2009 Lachaine et al.
2009/0036902 A1 2/2009 DeMaio et al.
2009/0105597 A1 4/2009 Abraham
2009/0118613 A1 5/2009 Krugman et al.
2009/0118724 A1 5/2009 Zvuloni et al.
2009/0118727 A1 5/2009 Pearson et al.
2009/0131783 A1 5/2009 Jenkins et al.
2009/0137907 A1 5/2009 Takimoto et al.
2009/0148008 A1 6/2009 Wiemker et al.
2009/0196480 A1 8/2009 Nields et al.
2009/0234369 A1 9/2009 Bax et al.
2009/0312629 A1 12/2009 Razzaque et al.
2010/0041949 A1 2/2010 Tolkowsky

(56) References Cited

U.S. PATENT DOCUMENTS

2010/0045783 A1 2/2010 State et al.
2010/0152570 A1 6/2010 Navab
2010/0185087 A1 7/2010 Nields et al.
2010/0198402 A1 8/2010 Greer et al.
2010/0208963 A1 8/2010 Kruecker et al.
2010/0268072 A1 10/2010 Hall et al.
2010/0268085 A1 10/2010 Kruecker et al.
2010/0296718 A1 11/2010 Ostrovsky-Berman et al.
2010/0298705 A1 11/2010 Pelissier et al.
2010/0305448 A1 12/2010 Dagonnau et al.
2010/0312121 A1 12/2010 Guan
2010/0331252 A1 12/2010 Hamrick
2011/0043612 A1 2/2011 Keller et al.
2011/0046483 A1 2/2011 Fuchs et al.
2011/0051083 A1 3/2011 Geggel
2011/0057930 A1 3/2011 Keller et al.
2011/0082351 A1 4/2011 Razzaque et al.
2011/0137156 A1 6/2011 Razzaque et al.
2011/0201915 A1 8/2011 Gogin et al.
2011/0201976 A1 8/2011 Sanghvi et al.
2011/0208055 A1 8/2011 Dalal et al.
2011/0230351 A1 9/2011 Fischer et al.
2011/0237947 A1 9/2011 Boctor et al.
2011/0238043 A1 9/2011 Kleven
2011/0274324 A1 11/2011 Clements et al.
2011/0282188 A1 11/2011 Burnside et al.
2011/0288412 A1 11/2011 Deckman et al.
2011/0295108 A1 12/2011 Cox et al.
2011/0301451 A1 12/2011 Rohling
2012/0035473 A1 2/2012 Sanghvi et al.
2012/0059260 A1 3/2012 Robinson
2012/0071759 A1 3/2012 Hagy et al.
2012/0078094 A1 3/2012 Nishina et al.
2012/0138658 A1 6/2012 Ullrich et al.
2012/0143029 A1 6/2012 Silverstein et al.
2012/0143055 A1 6/2012 Ng et al.
2012/0165679 A1 6/2012 Orome et al.
2012/0215096 A1 8/2012 Gilboa
2012/0230559 A1 9/2012 Itai
2012/0237105 A1 9/2012 Mielekamp
2012/0238857 A1 9/2012 Wong et al.
2012/0259210 A1 10/2012 Harhen et al.
2013/0030286 A1 1/2013 Alouani et al.
2013/0044930 A1 2/2013 Li et al.
2013/0079770 A1 3/2013 Kyle, Jr. et al.
2013/0090646 A1 4/2013 Moss et al.
2013/0096497 A1 4/2013 Duindam et al.
2013/0132374 A1 5/2013 Olstad et al.
2013/0144165 A1 6/2013 Ebbini et al.
2013/0151533 A1 6/2013 Udupa et al.
2013/0178745 A1 7/2013 Kyle et al.
2013/0197357 A1 8/2013 Green et al.
2013/0218024 A1 8/2013 Boctor et al.
2013/0249787 A1 9/2013 Morimoto
2014/0051987 A1 2/2014 Kowshik et al.
2014/0058387 A1 2/2014 Kruecker et al.
2014/0078138 A1 3/2014 Martin et al.
2014/0180074 A1 6/2014 Green
2014/0201669 A1 7/2014 Liu et al.
2014/0275760 A1 9/2014 Lee et al.
2014/0275810 A1 9/2014 Keller et al.
2014/0275997 A1 9/2014 Chopra et al.
2014/0350390 A1 11/2014 Kudavelly et al.
2015/0235373 A1 8/2015 Kato et al.
2015/0238259 A1 8/2015 Albeck et al.
2015/0257847 A1 9/2015 Higgins et al.
2016/0117857 A1 4/2016 State et al.
2016/0166334 A1 6/2016 Razzaque et al.
2016/0196694 A1 7/2016 Lindeman
2016/0228068 A1 8/2016 Hancu et al.
2016/0270862 A1 9/2016 Fuchs et al.
2016/0354152 A1 12/2016 Beck
2017/0024903 A1 1/2017 Razzaque et al.
2017/0099479 A1 4/2017 Browd et al.
2017/0325896 A1 11/2017 Donhowe et al.
2017/0340266 A1 11/2017 Gardner et al.
2017/0348067 A1 12/2017 Krimsky
2018/0289344 A1 10/2018 Green et al.
2020/0046315 A1 2/2020 State et al.
2021/0113273 A1 4/2021 State et al.
2021/0161601 A1 6/2021 State et al.
2022/0192611 A1 6/2022 Kohli et al.
2022/0296208 A1 9/2022 Kohli et al.
2023/0233264 A1 7/2023 State et al.
2024/0041536 A1 2/2024 State et al.
2024/0366314 A1 11/2024 Heaney et al.

FOREIGN PATENT DOCUMENTS

JP H07-116164 A 5/1995
WO WO 96/005768 2/1996
WO WO 97/015249 5/1997
WO WO 97/017014 5/1997
WO WO 97/029682 8/1997
WO WO 01/039683 6/2001

OTHER PUBLICATIONS

U.S. Appl. No. 15/068,323 including without limitation Office Actions, Amendments, Remarks, and any other potentially relevant documents, filed Mar. 11, 2016, Razzaque et al.

U.S. Appl. No. 17/652,785 including its ongoing prosecution history, including without limitation Office Actions, Amendments, Remarks, and any other potentially relevant documents, filed Feb. 28, 2022, Kohli et al.

U.S. Appl. No. 17/664,797 including without limitation Office Actions, Amendments, Remarks, and any other potentially relevant documents, filed May 24, 2022, State et al.

U.S. Appl. No. 18/045,115 including its ongoing prosecution history, including without limitation Office Actions, Amendments, Remarks, and any other potentially relevant documents, filed Oct. 7, 2022, State et al.

U.S. Appl. No. 18/048,711 including its ongoing prosecution history, including without limitation Office Actions, Amendments, Remarks, and any other potentially relevant documents, filed Oct. 21, 2022, Keller et al.

U.S. Appl. No. 18/051,399 including its ongoing prosecution history, including without limitation Office Actions, Amendments, Remarks, and any other potentially relevant documents, filed Oct. 31, 2022, Kohli et al.

U.S. Appl. No. 18/145,648 including its ongoing prosecution history, including without limitation Office Actions, Amendments, Remarks, and any other potentially relevant documents, filed Dec. 22, 2022, Heaney et al.

"3D Laparoscope Technology," http://www.inneroptic.com/tech_3DL.htm, copyright 2007 InnerOptic Technology, Inc. printed Sep. 19, 2007, 2 pages.

"AIM 3D Needle Placement Software from InnerOptic", Medgadget, Sep. 21, 2012.

AIM Section 5: 510k Summary, submitted by InnerOptic Technology, Inc., in 5 pages, submission date May 17, 2012.

"Cancer Facts & Figures 2004," www.cancer.org/downloads/STT/CAFF_finalPWSecured.pdf, copyright 2004 American Cancer Society, Inc., printed Sep. 19, 2007, 60 pages.

Cancer Prevention & Early Detection Facts & Figures 2004; National Center for Tobacco-Free Kids; 2004; American Cancer Society; USA.

"David Laserscanner <-Latest News <-Institute for Robotics and Process Control <-Te . . . ," http://www/rob.cs.tu-bs.de/en/news/david, printed Sep. 19, 2007, 1 page.

"InnerOptic's AIM System Receives Da 510(K) Clearance", InnerOptic Technology, Inc., Sep. 18, 2012.

"Laser scanned 3d model Final" video, still image of video attached, http://www.youtube.com/watch?v+DaLglgmoUf8, copyright 2007 YouTube, LLC, printed Sep. 19, 2007, 2 pages.

"Olympus Endoscopic Ultrasound System," www.olympusamerica.com/msg_section/download_brochures/135_b_gfum130.pdf, printed Sep. 20, 2007, 20 pages.

(56) References Cited

OTHER PUBLICATIONS

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.
"Robbins, Mike—Computer Vision Research—Stereo Depth Perception," http://www.compumike.com/vision/stereodepth. php, copyright 2007 Michael F. Robbins, printed Sep. 19, 2007, 3 pages.
"RUE, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com)., Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma et al., "Improving Static and Dynamic Registration in an Optical See-Through HMD," Paper Presented at SIGGRAPH '94 Annual Conference in Orlando, FL, 197-204; (1994).
Azuma, "A Survey of Augmented Reality," Presence: Teleoperators and Virtual Environments 6, 4:1-48 (Aug. 1997).
Badler et al., "Simulating Humans: Computer Graphics, Animation, and Control," Oxford University Press (1993).
Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.
Benavides et al., "Multispectral digital colposcopy for in vivo detection of cervical cancer," Optics Express; May 19, 2003; 11(1 0) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM),Banff, Alberta, Canada, Oct. 6-10, 2003, pp. 334-341, NRC 47083, copyright 2003 National Research Council of Canada, http:/iit-iti.nrc-cnrc.gc.ca/iit-publications-iti/docs/NRC-47083.pdf, printed Sep. 19, 2007, 9 pages.
Billinghurst, M. et al., Research Directions in Handheld AR; Int. J. of Virtual Reality 5(2), 51-58 (2006).
Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British Journal of Obstetrics and Gynecology; Dec. 1991; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue via Infrared Microscopy," Cellular and Molecular Biology; 1998; 44(1):219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Dumoulin, C.L. et al., Real-Time Position Monitoring of Invasive Devices Using Magnetic Resonance, Magnetic Resonance in Medicine, vol. 29, Issue 3, Mar. 1993, pp. 411-415.
Edwards et al., Video See-Through Design for Merging of Real and Virtual Environments, VRAIS '93, pp. 1-11 (1993).
Fahey et al., "Meta-analysis of Pap Test Accuracy; American Journal of Epidemiology," 1995 141(7):680-689; The John Hopkins University School of Hvqiene and Public Health; USA.
Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).
Fronheiser et al., Real-Time 3D Color Doppler for Guidance of Vibrating Interventional Devices, IEEE Ultrasonics Symposium, pp. 149-152 (2004).
Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_LaparoSurg98.pdf, printed Sep. 20, 2007, 10 pages.
Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.
Fuchs, et al.: "Virtual Environments Technology to Aid Needle Biopsies of the Breast," Health Care in the Information Age, Ch. 6, pp. 60-61, Presented in San Diego, Jan. 17-20, 1996, published by IOS Press and Ohmsha Feb. 1996.
Fuhrmann et al, Comprehensive calibration and registration procedures for augmented reality; Proc. Eurographics Workshop on Virtual Environments 2001, 219-228 (2001).
Garrett, William F. et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.
Georgakoudi et al., "Trimodal spectroscopy for the detection and characterization of cervical precancers in vivo," American Journal of Obstetrics and Gynecology; Mar. 2002; 186(3):374-382; USA.
StereoMirror Technology Webpage, http://www.planar.com/products/flatpanel_monitors/stereoscopic/ (Printed Dec. 29, 2011).
Herline et al., Surface Registration for Use in Interactive, Image-Guided Liver Surgery, Computer Aided Surgery 5:11-17 (2000).

(56) References Cited

OTHER PUBLICATIONS

Holloway, R .; Registration Error Analysis for Augmented Reality; Presence: Teleoperators and Virtual Environments 6(4), 413-432 (1997).
Hornung et al., "Quantitative near-infrared spectroscopy of cervical dysplasia in vivo," Human Reproduction; 1999; 14(11):2908-2916; European Society of Human Reproduction and Embryology.
Howard, M.D., et al.: "An Electronic Device for Needle Placement during Sonographically Guided Percutaneous Intervention", Radiology 2001; 218:905-911.
InnerAim Brochure; 3D Visualization Software for Simpler, Safer, more Precise Aiming, Published no earlier than Apr. 1, 2010.
InVision System Brochure; A "GPS" for Real-Time 3D Needle Visualization & Guidance, Published No. earlier than Mar. 1, 2008.
Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.
Jolesz, Ferenc A, M.D., et al. MRI-Guided Laser-Induced Interstitial Thermotherapy: BasicPrinciples, SPIE Institute on Laser-Induced Interstitial Thermotherapy (L1TT), Jun. 22-23, 1995, Berlin, Germany.
Kadi, A Majeed, et al., Design and Simulation of an Articulated Surgical Arm for Guiding SterotacticNeurosurgery, SPIE vol. 1708 Applications of Artificial Intelligence X: Machine Vision and Robotics (1992). Downloaded from: http://proceedings.spiedigitallibrary.org/ on Jul. 11, 2013.
Kanbara et al., "A Stereoscopic Video See-through Augmented Reality System Based on Real-time Vision-Based Registration," Nara Institute of Science and Technology, pp. 1-8 (2000).
Kato, Amami, et al., A frameless, armless navigational system for computer-assisted neurosurgery, Journal of Neurosurgery, vol. 74, No. 5, May 1991, pp. 845-849.
Keller et al., "What is it in Head Mounted Displays (MDs) that really make them all so terrible?," pp. 1-8 (1998).
Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.
Lee, et al., "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, 11(2):144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Lipton, "Foundations of the Steroscopic Cinema a Study in Depth," Van Nostrad Reinhold Company, pp. 1-319 (1982).
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).
Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.
Milgram et al., "Adaptation Effects in Stereo due to Online Changes in Camera Configuration," SPIE vol. 1669-13, Stereoscopic Displays and Applications III, 17 pages (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Ultrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95-023, (1993).
PCT, International Search Report and Written Opinion, re PCT Application No. PCT/US07/75122, mailing date Aug. 20, 2008.
PCT, International Preliminary Report on Patentability, re PCT Application No. PCT/US07/75122, mailing date Mar. 3, 2009.
Ohnesorge Lauren K., "InnerOptic technology wins FDA approval", Triangle Business Journal, Sep. 19, 2012.
Pogue, Brian W. et al., "Analysis of acetic acid-induced whitening of high-grade squamous intraepitheliallesions," Journal of Biomedical Optics; Oct. 2001; 6(4):397-403.
Press Release: Pathfinder and InnerOptic Announce Technology Integration to Enhance Visualization and Outcomes in Liver Surgery, Published Mar. 6, 2013.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging-Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
State et al., "Case Study: Observing a vol. Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.

(56) References Cited

OTHER PUBLICATIONS

State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking andMagnetic Tracking," ACM SIGGRAPH Computer Graphics, Proceedings of SIGGRAPH 1996, Annual Conference Series, 10 pages (Aug. 1996).
State et al., "Technologies for Augmented Reality Systems: Realizing Ultrasound-Guided NeedleBiopsies," Proc. SIGGRAPH 96 (New Orleans, LA, Aug. 4-9, 1996). In Computer Graphics Proceedings, Annual Conference Series, 1996, ACM SIGGRAPH, pp. 439-446.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takagi et al., "Development of a Stereo Video See-through HMD for AR Systems," IEEE, pp. 68-77 (2000).
Takayama et al., "Virtual Human with Regard to Physical Contact and Eye Contact," Entertaining Computing 2005, LNCS, vol. 3711, pp. 268-278 (2005).
Ultraguide 1000 System, Ultraguide, www.ultraguideinc.com, 1998.
Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 137-154 (1997).
Viola, Paul A., Alignment by Maximization of Mutual Information, Ph.D. Dissertation, MIT—Artificial Intelligence Laboratory Technical Report No. 1548 (Jun. 1995), 156 pages.
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, GRAPHITE 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).
Rieder, et al., "GPU-Based Real-Time Approximation of the Ablation Zone for Radiofrequency Ablatin," IEEE Transactions on Visualization and Computer Graphics 17.12 (2011): 1812-1821.

* cited by examiner

SYSTEM AND METHOD OF PROVIDING REAL-TIME DYNAMIC IMAGERY OF A MEDICAL PROCEDURE SITE USING MULTIPLE MODALITIES

RELATED APPLICATIONS

This application is a continuation of U.S. patent application Ser. No. 16/920,560, filed Jul. 3, 2020, entitled "System and Method of Providing Real-Time Dynamic Imagery of a Medical Procedure Site Using Multiple Modalities," which is a continuation of U.S. patent application Ser. No. 16/177,894, filed Nov. 1, 2018, entitled "System and Method of Providing Real-Time Dynamic Imagery of a Medical Procedure Site Using Multiple Modalities," which is a continuation U.S. patent application Ser. No. 15/598,616, filed May 18, 2017, entitled "System and Method of Providing Real-Time Dynamic Imagery of a Medical Procedure Site Using Multiple Modalities," which is a continuation of U.S. patent application Ser. No. 13/936,951, filed Jul. 8, 2013, entitled "System and Method of Providing Real-Time Dynamic Imagery of a Medical Procedure Site Using Multiple Modalities," which is a continuation of U.S. patent application Ser. No. 12/760,274, filed Apr. 14, 2010, entitled "System and Method of Providing Real-Time Dynamic Imagery of a Medical Procedure Site Using Multiple Modalities," which is a continuation of U.S. patent application Ser. No. 11/833,134, filed Aug. 2, 2007, entitled "System and Method of Providing Real-Time Dynamic Imagery of a Medical Procedure Site Using Multiple Modalities," which claims priority benefit to U.S. Provisional Application Ser. No. 60/834,932, filed Aug. 2, 2006, entitled "Spatially Registered Ultrasound and Endoscopic Imagery," and U.S. Provisional Application Ser. No. 60/856,670, filed Nov. 6, 2006, entitled "Multiple Depth-Reconstructive Endoscopies Combined With Other Medical Imaging Modalities, And System," the disclosure of each of which is hereby incorporated by reference in its entireties for all purposes.

BACKGROUND OF THE INVENTION

Field of the Invention

The present invention is directed to a system and method of providing composite real-time dynamic imagery of a medical procedure site using multiple modalities. One or more of the modalities may provide two-dimensional or three-dimensional imagery.

Description of the Related Art

It is well established that minimally-invasive surgery (MIS) techniques offer significant health benefits over their analogous laparotomic (or "open") counterparts. Among these benefits are reduced trauma, rapid recovery time, and shortened hospital stays, resulting in greatly reduced care needs and costs. However, because of limited visibility to certain internal organs, some surgical procedures are at present difficult to perform using MIS. With conventional technology, a surgeon operates through small incisions using special instruments while viewing internal anatomy and the operating field through a two-dimensional monitor. Operating below while seeing a separate image above can give rise to a number of problems. These include the issue of parallax, a spatial coordination problem, and a lack of depth perception. Thus, the surgeon bears a higher cognitive load when employing MIS techniques than with conventional open surgery because the surgeon has to work with a less natural hand-instrument-image coordination.

These problems may be exacerbated when the surgeon wishes to employ other modalities to view the procedure. A modality may be any method and/or technique for visually representing a scene. Such modalities, such as intraoperative laparoscopic ultrasound, would benefit the procedure by providing complementary information regarding the anatomy of the surgical site, and, in some cases, allowing the surgeon to see inside of an organ before making an incision or performing any other treatment and/or procedure. But employing more than one modality is often prohibitively difficult to use. This is particularly the case when the modalities are video streams displayed separately on separate monitors. Even if the different modalities are presented in a picture-in-picture or side-by-side arrangement on the same monitor, it would not be obvious to the surgeon, or any other viewer, how the anatomical features in each video stream correspond. This is so because, the spatial relationship between the areas of interest at the surgical site, for example, surface, tissue, organs, and/or other objects imaged by the different modalities, are not aligned to the same view perspectives. As such, the same areas of interest may be positioned and oriented differently between the different modalities. This is a particular problem for modalities like ultrasound, wherein anatomical features do not obviously correspond to the same feature in optical (or white-light) video.

The problems may be further exacerbated in that the surgical site is not static but dynamic, continually changing during the surgery. For example, in laparoscopic surgery, the organs in the abdomen continually move and reshape as the surgeon explores, cuts, stitches, removes and otherwise manipulates organs and tissues inside the body cavity. Even the amount of gas inside the body cavity (used to make space for the surgical instruments) changes during the surgery, and this affects the shape or position of everything within the surgical site. Therefore, if the views from the modalities are not continuous and immediate, they may not accurately and effectively depict the current state and/or conditions of the surgical site.

While there is current medical imaging technology that superimposes a video stream using one modality on an image dataset from another modality, the image dataset is static and, therefore, not continuous or immediate. As such, the image dataset, must be periodically updated based on the position of the subject, for example the patient, and/or anatomical or other features and/or landmarks. Periodically updating and/or modifying the image dataset may introduce undue latency in the system, which may be unacceptable from a medical procedure standpoint. The undue latency may cause the image being viewed on the display by the surgeon to be continually obsolete. Additionally, relying on the positions of the subject, and/or anatomical or other features and/or landmarks to update and/or modify the image being viewed, may cause the images from the different modalities to not only be obsolete but, also, non-synchronous when viewed.

Accordingly, there currently is no medical imaging technology directed to providing composite real-time dynamic imagery from multiple modalities using two or more video streams, wherein each video stream from each modality may provide a real-time view of the medical procedure site to provide a continuous and immediate view of the current state and condition of the medical procedure site. Also, there currently is no medical imaging technology directed to providing composite imagery from multiple modalities using two or more video streams, wherein each video stream may be dynamic in that each may be synchronized to the other, and not separately to the position of the subject, and/or anatomical or other features and/or landmarks. As such, there is currently no medical imaging technology that provides composite real-time, dynamic imagery of the medical procedure site from multiple modalities.

Therefore, there is a need for a system and method of providing composite real-time dynamic imagery of a medical procedure site from multiple medical modalities, which continuously and immediately depicts the current state and condition of the medical procedure site and does so synchronously with respect to each of the modalities and without undue latency.

SUMMARY OF THE INVENTION

The present invention is directed to a system and method of providing composite real-time dynamic imagery of a medical procedure site from multiple modalities which continuously and immediately depicts the current state and condition of the medical procedure site synchronously with respect to each modality and without undue latency. The composite real-time dynamic imagery may be provided by spatially registering multiple real-time dynamic video streams from the multiple modalities to each other. Spatially registering the multiple real-time dynamic video streams to each other may provide a continuous and immediate depiction of the medical procedure site with an unobstructed and detailed view of a region of interest at the medical procedure site. As such, a surgeon, or other medical practitioner, may view a single, accurate, and current composite real-time dynamic imagery of a region of interest at the medical procedure site as he/she performs a medical procedure, and thereby, may properly and effectively implement the medical procedure.

In this regard, a first real-time dynamic video stream of a scene based on a first modality may be received. A second real-time dynamic video stream of the scene based on a second modality may also be received. The scene may comprise tissues, bones, instruments, and/or other surfaces or objects at a medical procedure site and at multiple depths. The first real-time dynamic video stream and the second real-time dynamic video stream may be spatially registered to each other. Spatially registering the first real-time dynamic video stream and the second real-time dynamic video stream to each other may form a composite representation of the scene. A composite real-time dynamic video stream of the scene may be generated from the composite representation. The composite real-time dynamic video stream may provide a continuous and immediate depiction of the medical procedure site with an unobstructed and detailed view at multiple depths of a region of interest at the medical procedure site. The composite real-time dynamic video stream may be sent to a display.

The first real-time dynamic video stream may depict the scene from a perspective based on a first spatial state of a first video source. Also, the second real-time dynamic video stream may depict the scene from a perspective based on a second spatial state of a second video source. The first spatial state may comprise a displacement and an orientation of the first video source, while the second spatial state may comprise a displacement and an orientation of the second video source. The first spatial state and the second spatial state may be used to synchronously align a frame of the second real-time dynamic video stream depicting a current perspective of the scene with a frame of the first real-time dynamic video stream depicting a current perspective of the scene. In this manner, the displacement and orientation of the first video source and the displacement and orientation of the second video source may be used to accurately depict the displacement and orientation of the surfaces and objects in the scene from both of the current perspectives in the composite representation.

The first modality may be two-dimensional or three-dimensional. Additionally, the first modality may comprise endoscopy, and may be selected from a group comprising laparoscopy, hysteroscopy, thoracoscopy, arthroscopy, colonoscopy, bronchoscopy, cystoscopy, proctosigmoidoscopy, esophagogastroduodenoscopy, and colposcopy. The second modality may be two-dimensional or three dimensional. Additionally, the second modality may comprise one or more modalities selected from a group comprising medical ultrasonography, magnetic resonance, x-ray imaging, computed tomography, and optical wavefront imaging. As such, a plurality, comprising any number, of video sources, modalities, and real-time dynamic video streams is encompassed by the present invention.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the invention, and together with the description serve to explain the principles of the invention.

DETAILED DESCRIPTION OF THE PREFERRED EMBODIMENT

Figure 1:
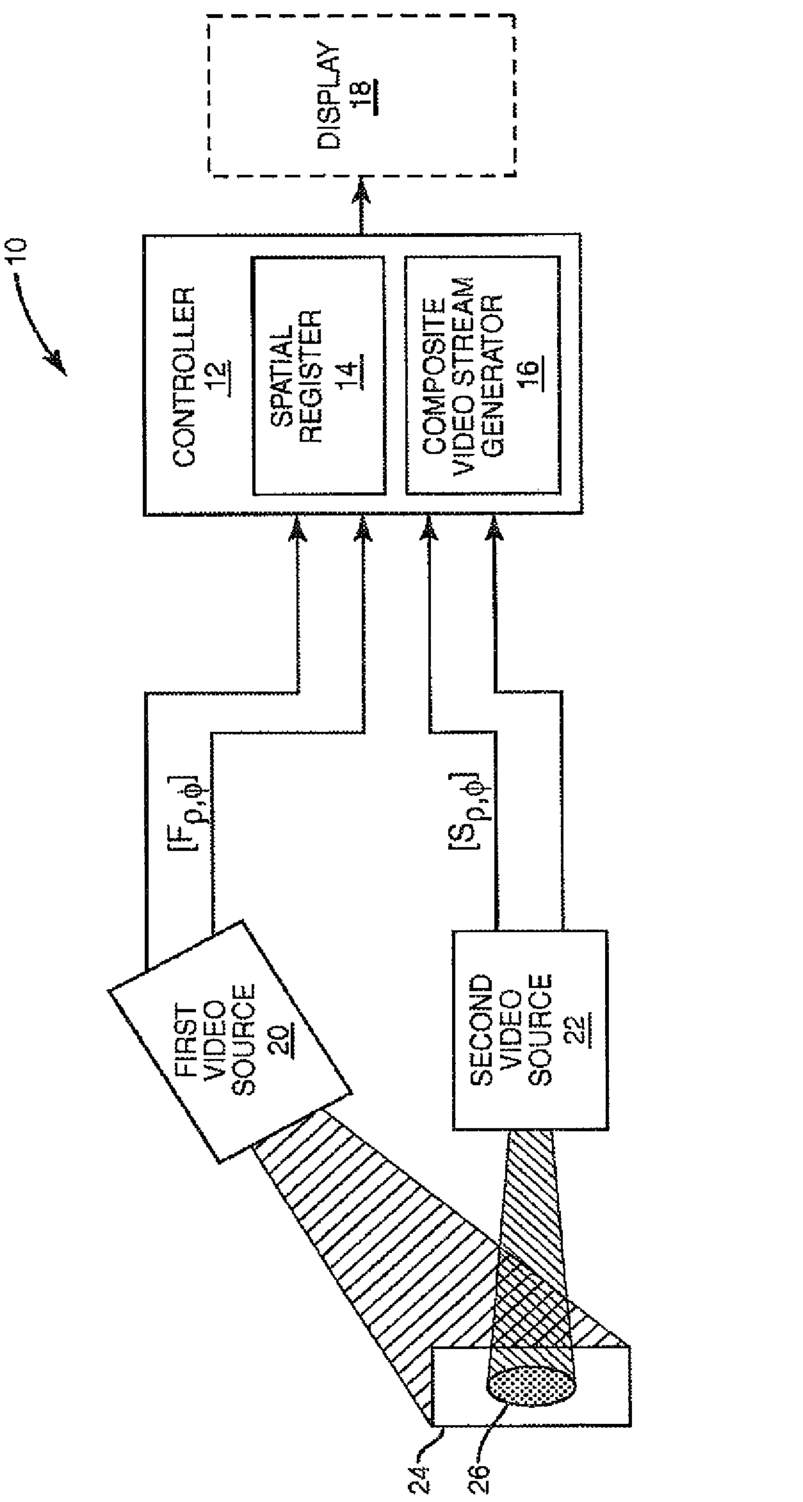
FIG. 1 is a schematic diagram illustrating an exemplary real-time dynamic imaging system, wherein a first real-time, dynamic video stream of a scene may be received from a first video source, and a second real-time dynamic video stream of the scene may be received from a second video source, and wherein the first real-time dynamic video stream and the second real-time dynamic video stream may be spatially registered to each other, according to an embodiment of the present invention.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention is directed to a system and method of providing composite real-time, dynamic imagery of a medical procedure site from multiple modalities which continuously and immediately depicts the current state and condition of the medical procedure site synchronously with respect to each modality and without undue latency. The composite real-time dynamic imagery may be provided by spatially registering multiple real-time dynamic video streams from the multiple modalities to each other. Spatially registering the multiple real-time dynamic video streams to each other may provide a continuous and immediate depiction of the medical procedure site with an unobstructed and detailed view of a region of interest at the medical procedure site. As such, a surgeon, or other medical practitioner, may view a single, accurate, and current composite real-time dynamic imagery of a region of interest at the medical procedure site as he/she performs a medical procedure, and thereby, may properly and effectively implement the medical procedure.

In this regard, a first real-time dynamic video stream of a scene based on a first modality may be received. A second real-time dynamic video stream of the scene based on a second modality may also be received. The scene may comprise tissues, bones, instruments, and/or other surfaces or objects at a medical procedure site and at multiple depths. The first real-time dynamic video stream and the second real-time dynamic video stream may be spatially registered to each other. Spatially registering the first real-time dynamic video stream and the second real-time dynamic video stream to each other may form a composite representation of the scene. A composite real-time dynamic video stream of the scene may be generated from the composite representation. The composite real-time dynamic video stream may provide a continuous and immediate depiction of the medical procedure site with an unobstructed and detailed view at multiple depths of a region of interest at the medical procedure site. The composite real-time dynamic video stream may be sent to a display.

The first real-time dynamic video stream may depict the scene from a perspective based on a first spatial state of a first video source. Also, the second real-time dynamic video stream may depict the scene from a perspective based on a second spatial state of a second video source. The first spatial state may comprise a displacement and an orientation of the first video source, while the second spatial state may comprise a displacement and an orientation of the second video source. The first spatial state and the second spatial state may be used to synchronously align a frame of the second real-time dynamic video stream depicting a current perspective of the scene with a frame of the first real-time dynamic video stream depicting a current perspective of the scene. In this manner, the displacement and orientation of the first video source and the displacement and orientation of the second video source may be used to accurately depict the displacement and orientation of the surfaces and objects from both of the current perspectives in the composite representation.

The first modality may be two-dimensional or three-dimensional. Additionally, the first modality may comprise endoscopy, and may be selected from a group comprising laparoscopy, hysteroscopy, thoracoscopy, arthroscopy, colonoscopy, bronchoscopy, cystoscopy, proctosigmoidoscopy, esophagogastroduodenoscopy, and colposcopy. The second modality may be two-dimensional or three dimensional. Additionally, the second modality may comprise one or more modalities selected from a group comprising medical ultrasonography, magnetic resonance, x-ray imaging, computed tomography, and optical wavefront imaging. As such, a plurality, comprising any number, of video sources, modalities, and real-time dynamic video streams is encompassed by embodiments of the present invention. Therefore, the first imaging modality may comprise a plurality of first imaging modalities and the second imaging modality may comprise a plurality of second imaging modalities.

Figure 2:
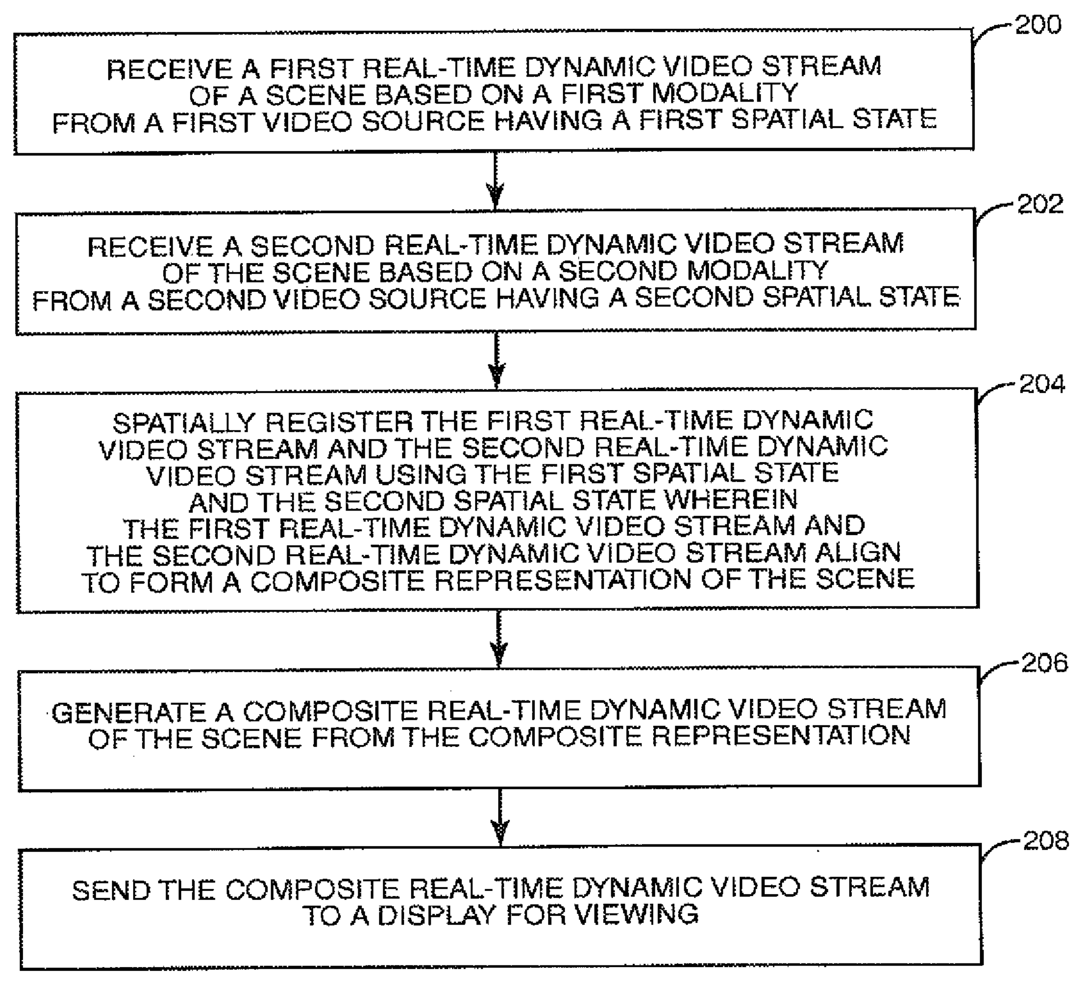
FIG. 2 is a flow chart illustrating a process for generating a composite real-time dynamic video stream of the scene by spatially registering the first real-time dynamic video stream and the second real-time dynamic video stream according to an embodiment of the present invention.

FIG. 1 illustrates a schematic diagram of an exemplary real-time dynamic imagery system 10 for generating a composite real-time dynamic video stream of a scene from a first real-time dynamic video stream based on a first modality and a second real-time dynamic video stream based on a second modality, according to an embodiment of the present invention. FIG. 2 is a flow chart illustrating a process for generating the composite real-time dynamic video stream of a scene in the system 10 according to an embodiment of the present invention. Using a first real-time dynamic video stream based on a first modality and a second real-time dynamic video stream based on a second modality to generate a composite real-time dynamic video stream may provide a continuous and immediate depiction of the current state and condition of the scene, and at multiple depths and with unobstructed depiction of details of the scene at those depths. For purposes of the embodiment of the present invention, immediate may be understood to be 500 milliseconds or less.

Accordingly, as the scene changes the first real-time dynamic video stream and the second real-time dynamic video stream may also change, and, as such, the composite real-time dynamic video stream may also change. As such, the composite real-time dynamic video stream may be immediate in that when viewed on a display, the composite real-time dynamic video stream may continuously depict the actual current state and/or condition of the scene and, therefore, may be suitable for medical procedure sites, including, but not limited to, surgical sites. By viewing a single, accurate, and current image of the region of interest, the surgeon, or the other medical practitioner, may properly and effectively implement the medical procedure while viewing the composite real-time dynamic imagery.

In this regard, the system 10 of FIG. 1 may include a controller 12 which may comprise a spatial register 14 and a composite video stream generator 16. The controller 12 may be communicably coupled, to a display 18, a first video source 20, and a second video source 22. The first video source 20 and the second video source 22 may comprise an instrument through which an image of the scene may be captured and/or detected. Accordingly, the first video source 20 and the second video source 22 capture and/or detect images of the scene from their particular perspectives. The first video source 20 may have a first spatial state and the second video source 22 may have a second spatial state. In this manner, the first spatial state may relate to the perspective in which the image is captured and/or detected by the first video source 20, and the second spatial state may relate to the perspective in which the image is captured and/or detected by the second video source 22.

The first spatial state may be represented as $[F_{\rho,\Phi}]$, and the second spatial state may be represented as $[S_{\rho,\Phi}]$. In FIG. 1, "ρ" may refer to three-dimensional displacement representing x, y, z positions, and "Φ" may refer to three-dimensional orientation representing roll, pitch, and yaw, with respect to both the first video source 20 and the second video source 22, as the case may be. By employing $[F_{\rho,\Phi}]$ and $[S_{\rho,\Phi}]$, the perspective of the first video source 20 viewing the scene and the perspective of the second video source 22 viewing the scene may be related to the three-dimensional displacement "ρ" and the three-dimensional orientation "Φ" of the first video source 20 and the second video source 22, respectively.

Accordingly, the first video source 20 and the second video source 22 capture and/or detect images of the scene from their particular perspectives. The scene may comprise a structure 24, which may be an organ within a person's body, and a region of interest 26 within the structure 24. The region of interest 26 may comprise a mass, lesion, growth, blood vessel, and/or any other condition and/or any detail within the structure 24. The region of interest 26 may or may not be detectable using visible light. In other words, the region of interest 26 may not be visible to the human eye.

The first video source 20 produces the first real-time dynamic video stream of the scene, and the second video source produces the second real-time dynamic video stream of the scene. The first real-time dynamic video stream of the scene may be a two-dimensional or three-dimensional video stream. Similarly, the second real-time dynamic video stream of the scene may be a two-dimensional or three-dimensional video stream.

FIG. 2 illustrates the process for generating a composite real-time dynamic video stream of the scene that may be based on the first real-time dynamic video stream and the second real-time dynamic video stream according to an embodiment of the present invention. The controller 12 may receive the first real-time dynamic video stream of a scene based on a first modality from a first video source having a first spatial state (step 200). The first modality may for example comprise two-dimensional or three-dimensional endoscopy. Additionally, the first modality may be any type of endoscopy such as laparoscopy, hysteroscopy, thoracoscopy, arthroscopy, colonoscopy, bronchoscopy, cystoscopy, proctosigmoidoscopy, esophagogastroduodenoscopy, and colposcopy. The controller 12 also may receive the second real-time dynamic video stream of the scene based on a second medical modality from a second video source having a second spatial state (step 202). The second modality may comprise one or more of two-dimensional or three-dimensional medical ultrasonography, magnetic resonance imaging, x-ray imaging, computed tomography, and optical wavefront imaging. Accordingly, the present invention is not limited to only two video sources using two modalities to produce only two real-time dynamic video streams. As such, a plurality, comprising any number, of video sources, modalities, and real-time dynamic video streams is encompassed by the present invention.

The controller 12 using the spatial register 14 may then spatially register the first real-time dynamic video stream and the second real-time dynamic video stream using the first spatial state and the second spatial state to align the first real-time dynamic video stream and the second real-time dynamic video stream to form a real-time dynamic composite representation of the scene (step 204). The controller 12 using the composite video stream generator 16 may generate a composite real-time dynamic video stream of the scene from the composite representation (step 206). The controller 12 may then send the composite real-time dynamic video stream to a display 18.

Please note that for purposes of discussing the embodiments of the present invention, it should be understood that the first video source 20 and the second video source 22 may comprise an instrument through which an image of the scene may be captured and/or detected. In embodiments of the present invention in which an imaging device such as a camera, for example, may be fixably attached to the instrument, the first video source 20 and the second video source 22 may be understood to comprise the imaging device in combination with the instrument. In embodiments of the present invention in which the imaging device may not be fixably attached to the instrument and, therefore, may be located remotely from the instrument, the first video source 20 and the second video source 22 may be understood to comprise the instrument and not the imaging device.

Figures 3A, 3B, 3C:
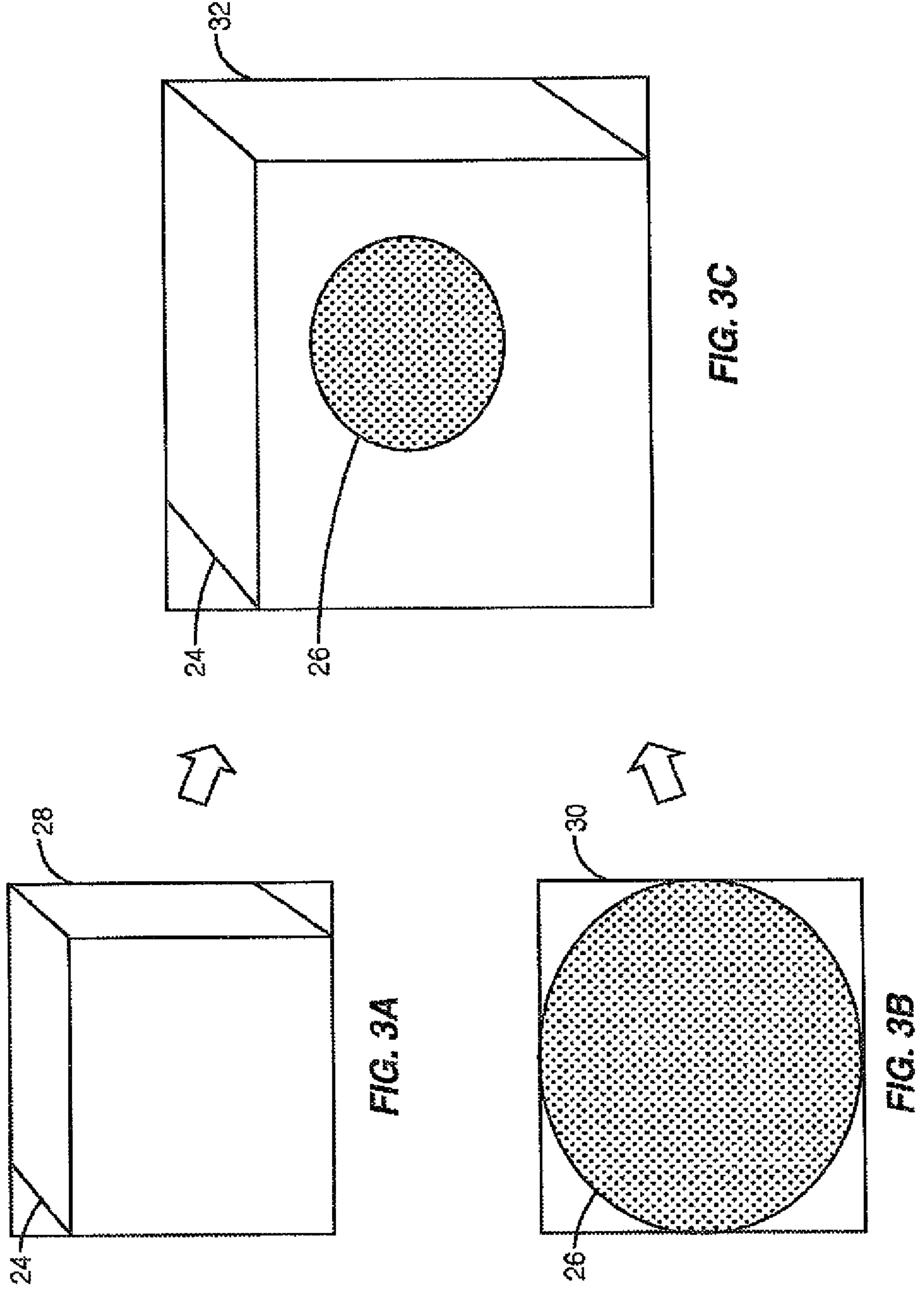
FIGS. 3A, 3B, and 3C are graphical representations of the spatial registering of a frame of the first real-time dynamic video stream and a frame of the second real-time dynamic video stream to form a composite representation of the scene, according to an embodiment of the present invention.

Spatially registering the first real-time dynamic video stream and the second real-time dynamic video stream may result in a composite real-time dynamic video stream that depicts the scene from merged perspectives of the first video source 20 and the second video source 22. FIGS. 3A, 3B, and 3C illustrate graphical representations depicting exemplary perspective views from the first video source 20 and the second video source 22, and a sequence which may result in the merged perspectives of the first real-time dynamic video stream and the second real-time dynamic video stream, according to an embodiment of the present invention. FIGS. 3A, 3B, and 3C provide a graphical context for the discussion of the computation involving forming the composite representation, which results from the spatial registration of the first real-time dynamic video stream and the second real-time dynamic video stream.

FIG. 3A may represent the perspective view of the first video source 20, shown as first frame 28. FIG. 3B may represent the perspective view of the second video source 22, shown as second frame 30. FIG. 3C shows the second frame 30 spatially registered with the first frame 28 which may represent a merged perspective and, accordingly, a composite representation 32, according to an embodiment of the present invention. The composite real-time dynamic video stream may be generated from the composite representation 32. Accordingly, the composite representation may provide the merged perspective of the frame of the scene depicted by the composite real-time dynamic video stream.

The first frame 28 may show the perspective view of the first video source 20 which may use a first medical modality, for example endoscopy. The first frame 28 may depict the outside of the structure 24. The perspective view of the structure 24 may fill the first frame 28. In other words, the edges of the perspective view of the structure 24 may be co-extensive and/or align with the corners and sides of the first frame 28. The second frame 30 may show the perspective view of the second video source 22 which may be detected using a second medical modality, for example medical ultrasonography. The second frame 30 may depict the region of interest 26 within the structure 24. As with the perspective view of the structure in the first frame 28, the perspective view of the region of interest 26 may fill the second frame 30. The edges of the region of interest 26 may be co-extensive and/or align with the sides of the second frame 30.

Because the perspective view of the structure 24 may fill the first frame 28, and the perspective view of the region of interest 26 may fill the second frame 30, combining the first frame 28 as provided by the first video source 20 with the second frame 30 as provided by the second video source 22 may not provide a view that accurately depicts the displacement and orientation of the region of interest 26 within the structure 24. Therefore, the first frame 28 and the second frame 30 may be synchronized such that the composite representation 32 accurately depicts the actual displacement and orientation of the region of interest 26 within the structure 24. The first frame 28 and the second frame 30 may be synchronized by determining the spatial relationship between the first video source 20 and the second video source 22 based on the first spatial state and the second spatial state. Accordingly, if the first spatial state and/or the second spatial state change, the first frame 28 and/or the second frame 30 may be synchronized based on the changed first spatial state and/or changed the second spatial state. In FIG. 3C, the first frame 28 and the second frame 30 may be synchronized by adjusting the second frame 30 to be co-extensive and/or aligned with the corners and the sides of the first frame 28. The spatial relationship may then be used to spatially register the second frame 30 with the first frame 28 to form the composite representation 32. The composite representation 32 may then depict the actual displacement and orientation of the region of interest 26 within the structure 24 synchronously with respect to the first real-time dynamic video stream and the second real-time video stream.

Spatially registering the first real-time dynamic video stream and the second real-time dynamic video stream may be performed using calculations involving the first spatial state of the first video source 20, and the second spatial state of the second video source 22. The first spatial state and the second spatial state each comprise six degrees of freedom. The six degrees of freedom may comprise a displacement representing x, y, z positions which is collectively referred to herein as "ρ," and orientation representing roll, pitch, and yaw which is collectively referred to herein as "Φ." Accordingly, the first spatial state may be represented as $[F_{\rho,\Phi}]$, and the second spatial state may be represented as $[S_{\rho,\Phi}]$. The first special state and the second spatial state may be used to determine the spatial relationship between the first video source 20 and the second video source 22, which may be represented as $[C_{\rho,\Phi}]$.

The first spatial state $[F_{\rho,\Phi}]$ may be considered to be a transformation between the coordinate system of the first video source 20 and some global coordinate system G, and the second spatial state $[S_{\rho,\Phi}]$ may be considered to be a transformation between the coordinate system of the second video source 22 and the same global coordinate system G. The spatial relationship $[C_{\rho,\Phi}]$, then, may be considered as a transformation from the coordinate system of the second video source 22, to the coordinate system of the first video source 20.

As transforms, $[C_{\rho,\Phi}]$, $[F_{\rho,\Phi}]$, and $[S_{\rho,\Phi}]$ may each be represented in one of three equivalent forms:

1) Three-dimensional displacement "ρ" as [tx, ty, tz] and three-dimensional orientation "Φ" as [roll, pitch, yaw]; or
2) Three-dimensional displacement "ρ" as [tx, ty, tz] and three-dimensional orientation "Φ" as a unit quaternion [qx, qy, qz, qw]; or
3) A 4-by-4 (16 element) matrix.

Form 1 has the advantage of being easiest to use. Form 2 has the advantage of being subject to less round-off error during computations, for example it avoids gimbal lock, a mathematical degeneracy problem. Form 3 is amendable to modern computer-graphics hardware, which has dedicated machinery for composing, transmitting, and computing 4-by-4 matrices.

In some embodiments, where the first video source 20 and second video source 22 do not move with respect to each other, the spatial relationship $[C_{\rho,\Phi}]$ between the first video source 20 and the second video source 22 is constant and may be measured directly. Alternatively, if embodiments where the first video source 20 and the second video source 22 move relative to each other, the spatial relationship between the first video source 20 and the second video source 22 may be continually measured by a position detecting system. The position detecting system may measure an output $[C_{\rho,\Phi}]$ directly, or it may measure and report the first spatial state $[F_{\rho,\Phi}]$, the second spatial state $[S_{\rho,\Phi}]$. In the latter case, $[C_{\rho,\Phi}]$ can be computed as $[C_{\rho,\Phi}]$ and $[C_{\rho,\Phi}]$ as follows:

$$[C_{\rho,\Phi}]=[F_{\rho,\Phi}]^{*}[S]^{-1}\text{(indirect computation).}$$

The three-dimensional position of the corner points of the second frame 30, relative to the center of the second frame 30, are constants which may be included in the specification sheets of the second video source 22. There are four (4) such points if the second video source 22 is two-dimensional, and eight (8) such points if the second video source 22 is three-dimensional. For each such corner point, three-dimensional position relative to the first video source 20 may be computed using the formula:

$$c_s=c_f{}^{*}[C_{\rho,\Phi}],$$

where $c_f$ is the second frame 30 corner point relative to the second video source 22, and $c_s$ is the second frame 30 corner point relative to first video source 20. If either the first video source 20 or the second video source 22 comprise a video camera, then the field-of-view of the video camera, and the frame, may be given by the manufacturer. The two-dimensional coordinates of the corner points ($s_x$, $s_y$) of the second frame 30 in the first frame 28 may be computed as follows:

$$C_{sp} = (C_s * [P]),$$

where $$P = \begin{bmatrix} \cos(f) & 0 & 0 & 0 \\ 0 & & 0 & 0 \\ 0 & 0 & 0 & 0 \\ 0 & 0 & 1 & 0 \end{bmatrix}$$

and f=the field of view of the first video source 20. $c_{sp}$ is a four (4) element homogenous coordinate consisting of [$x_{csp}$, $y_{csp}$, $z_{csp}$, $h_{csp}$]. The two-dimensional coordinates are finally computed as:

$$s_x = x_{csp} / h_{csp}; \text{ and}$$

$$s_y = y_{csp} / h_{csp}$$

By knowing $s_x$ and $s_y$, for all the corners of the second frame 30 relative to the first frame 28 standard compositing hardware may be used to overlay and, thereby, spatially registering the first real-time dynamic video stream and the second real-time dynamic video stream to generate the composite real-time dynamic video stream. As such the spatial registration of the first real-time dynamic video stream and the second real-time dynamic video stream may be performed using information other than an anatomical characteristic and/or a position of the subject (i.e. a person's body), the world, or some other reference coordinate system. Accordingly, the composite real-time dynamic video stream may be generated independently of the position or condition of the subject, the location and/or existence of anatomical features and/or landmarks, and/or the condition or state of the medical procedure site.

The determination whether to directly or indirectly compute the spatial relationship between the first video source 20 and the second video source 22 may depend on an arrangement of components of the system, and a method used to establish the first spatial state of the first video source 20 and the second spatial state of the second video source 22.

Figures 4A, 4B:
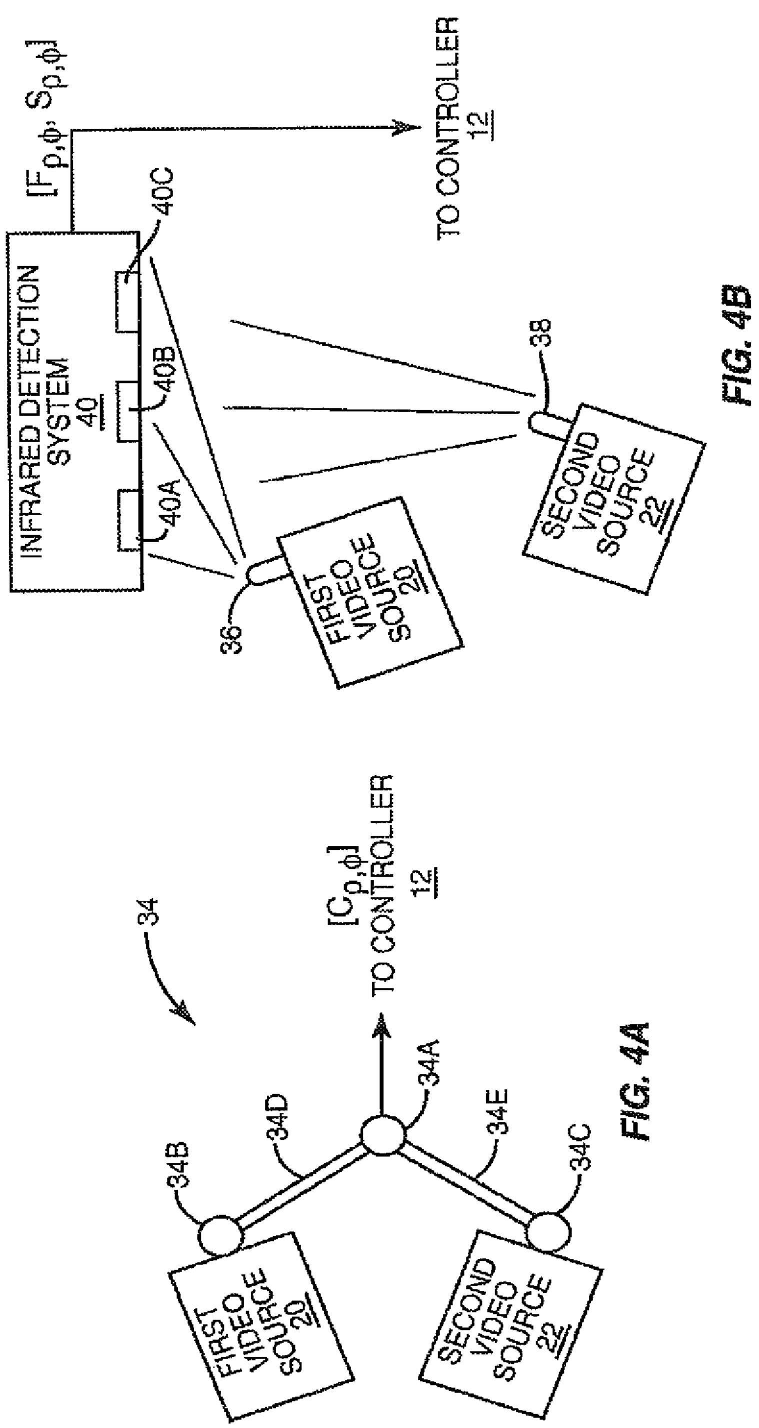
FIGS. 4A and 4B illustrate exemplary arrangements, which may be used to determine the spatial relationship between the first video source and the second video source using the first spatial state and the second spatial state, according to an embodiment of the present invention.

FIGS. 4A and 4B are schematic diagrams illustrating alternative exemplary arrangements of components in which the direct computation or the indirect computation for determining the spatial relationship between the first video source 20 and the second video source 22 may be used.

FIG. 4A illustrates an exemplary arrangement in which the direct computation of the spatial relationship between the first video source 20 and the second video source 22 may be used, according to an embodiment of the present invention. An articulated mechanical arm 34 may connect the first video source 20 and the second video source 22. The mechanical arm 34 may be part of and/or extend to an instrument or other structure, which supports and/or allows the use of the mechanical arm 34, and thereby the first video source 20 and the second video source 22. The mechanical arm 34 may provide a rigid connection between the first video source 20 and the second video source 22. In such a case, because the mechanical arm may be rigid, the first spatial state of the first video source 20 and the second spatial state of the second video source 22 may be fixed.

Accordingly, because the first spatial state and the second spatial state may be fixed, the first spatial state and the second spatial state may be programmed or recorded in the controller 12. The controller 12 may then directly compute the spatial relationship between the first video source 20 and the second video source 22 and, therefrom, the composite representation 32. As discussed above, the composite representation 32 represents the spatial registration of the first real-time dynamic video stream and the second real-time dynamic video stream. The controller 12 may then generate the composite real-time dynamic video stream from the composite representation 32.

Alternatively, the mechanical arm 34 may comprise joints 34A, 34B, 34C connecting rigid portions or links 34D, 34E of the mechanical arm 34. The joints 34A, 34B, 34C may include rotary encoders for measuring and encoding the angle of each of the joints 34A, 34B, 34C. By measuring the angle of the joints 34A, 34B, 34C and knowing the length of the links 34D, 34E, the first spatial state [$C_{\rho,\Phi}$] of the second video source 22, relative to that of the first video source 20 may be determined. The controller 12 may receive [$C_{\rho,\Phi}$)] and, therefrom, compute the composite representation 32. As discussed above, the composite representation 32 represents the spatial registration of the first real-time dynamic video stream and the second real-time dynamic video stream. The controller 12 may generate the composite real-time dynamic video stream from the composite representation. The mechanical arm 34 may be a Faro-Arm™. mechanical arms or any similar component that provides the functionality described above.

FIG. 4B illustrates an exemplary arrangement where the indirect computation of the spatial relationship between the first video source 20 and the second video source 22 may be used, according to an embodiment of the present invention. In FIG. 4B, an intermediary in the form of a positions detecting system comprising a first transmitter 36, a second transmitter 38, and an infrared detection system 40 are shown. The first transmitter 36 and the second transmitter 38 may be in the form of LED's. The infrared detection system 40 may comprise one or more infrared detectors 40A, 40B, 40C. The infrared detectors 40A, 40B, 40C may be located or positioned to be in lines-of-sight of the first transmitter 36 and the second transmitter 38. The lines-of-sight are shown in FIG. 4B by lines emanating from the first transmitter 36 and the second transmitter 38.

The infrared detection system 40 may determine the first spatial state of the first video source 20 and the second spatial state of the second video source 22 by detecting the light emitted from the first transmitter 36 and the second transmitter 38, respectively. The infrared detection system 40 may also determine the intermediary reference related to the position of the infrared detection system 40. The infrared detection system 40 may then send the first spatial state of the first video source 20, represented as [$F_{\rho,\Phi}$], and the second spatial state of the second video source 22, represented as [$S_{\rho,\Phi}$], to the controller 12. The controller 12 may receive the first spatial state and the second spatial state, and may compute the spatial relationship [$C_{\rho,\Phi}$] between the first video source 20 and the second video source 22 using the indirect computation and, therefrom, the composite representation 32. As discussed above, the composite representation 32 represents the spatial registration of the first real-time dynamic video stream and the second real-time dynamic video stream. The controller 12 may then generate the composite real-time dynamic video stream from the composite representation 32.

The infrared detection system 40 may be any type of optoelectronic system for example the Northern Digital Instrument Optotrak™. Alternatively, other position detecting systems may be used such as magnetic, GPS+compass, inertial, acoustic, or any other equipment for measuring spatial relationship, or relative or absolute displacement and orientation.

Figure 5:
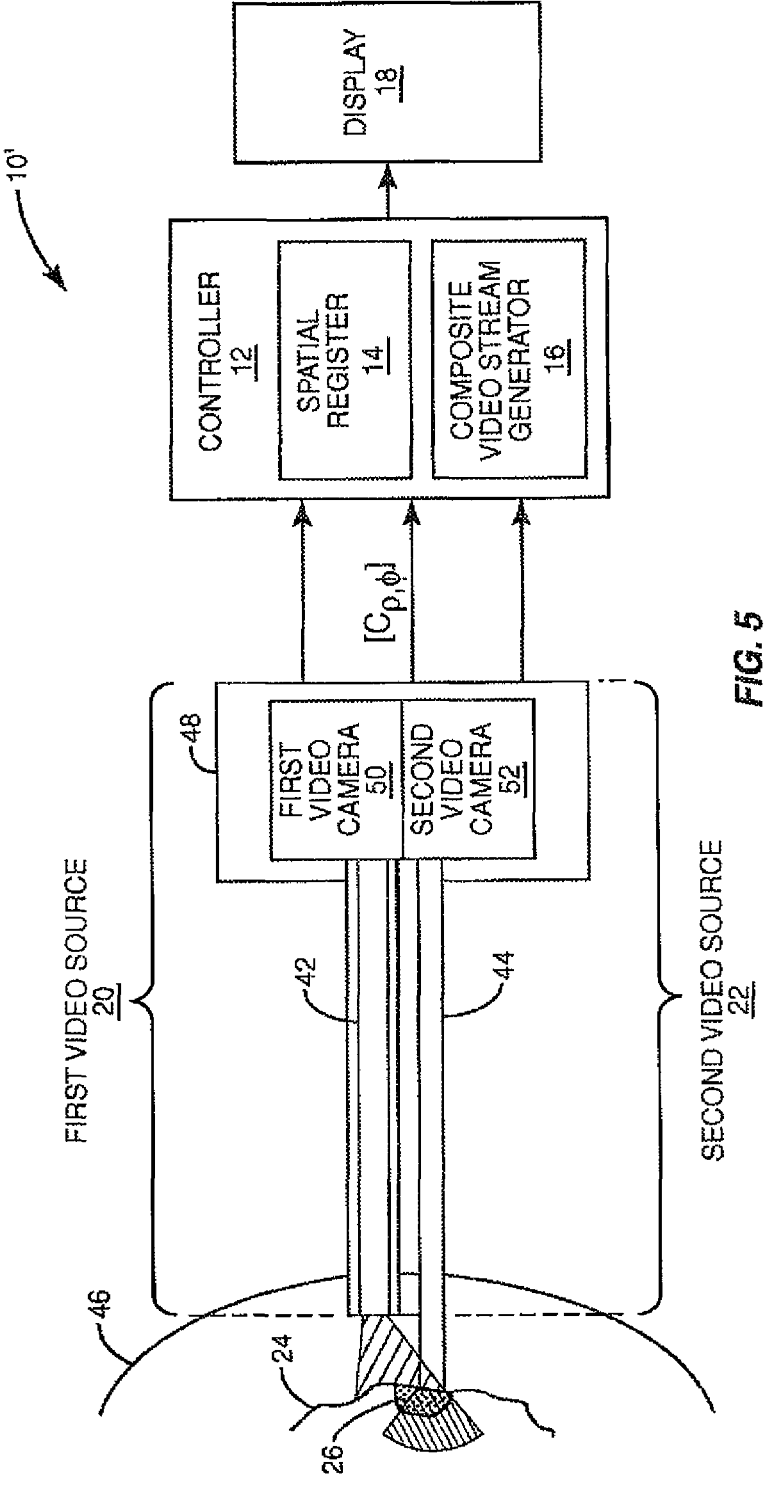
FIG. 5 is a schematic diagram illustrating an exemplary real-time dynamic imaging system at a medical procedure site, wherein the first video source and the second video source are co-located, and wherein the first video source may comprise an endoscope, and wherein the second video source may comprise an ultrasound transducer, according to an embodiment of the present invention.
Figure 6:
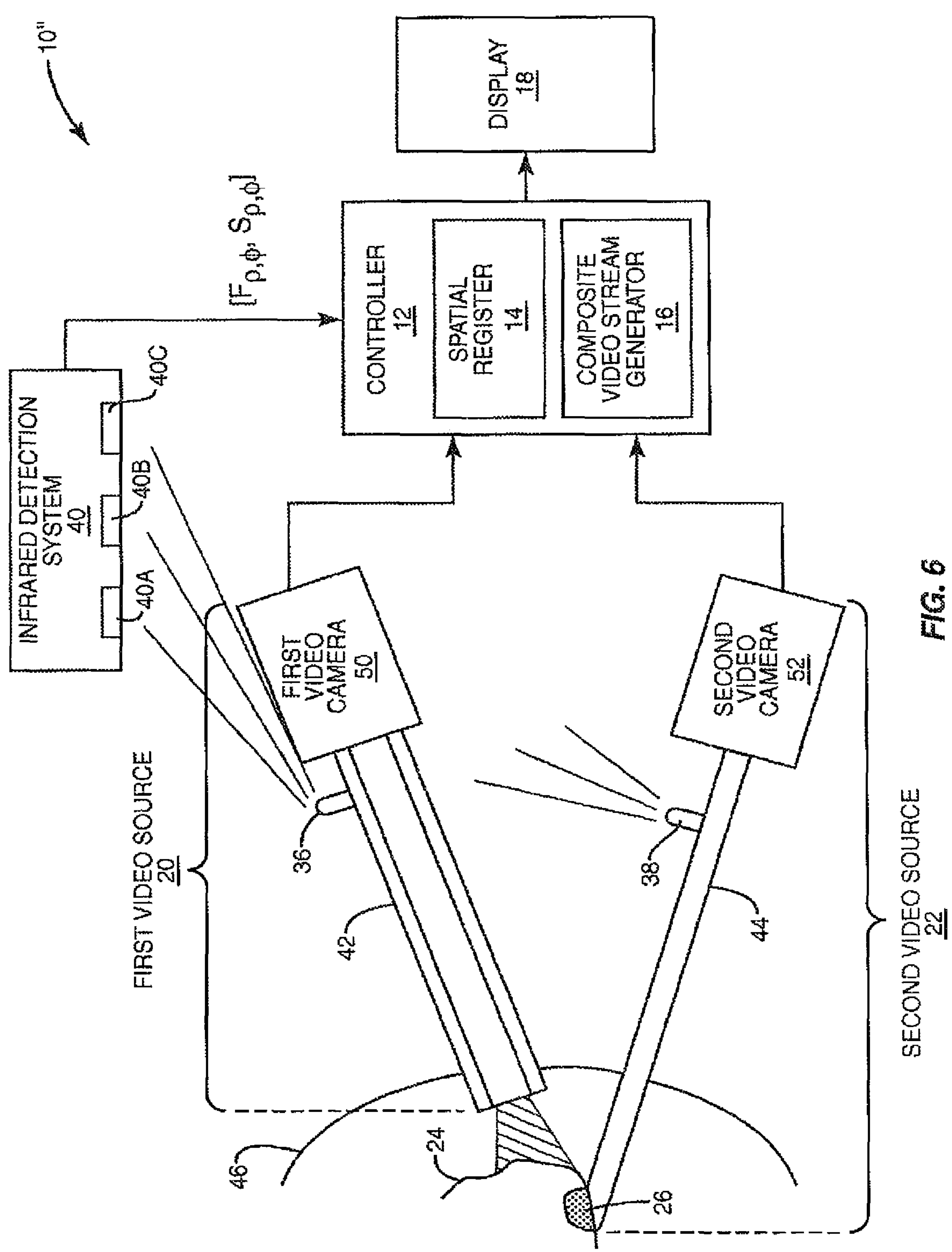
FIG. 6 is a schematic diagram illustrating an exemplary real-time dynamic imaging system at a medical procedure site wherein the first video source and the second video source are separately located and wherein an infrared detection system to determine the first spatial state and the second spatial state may be included, according to an embodiment of the present invention.

FIGS. 5 and 6 are schematic diagrams illustrating exemplary systems in which the exemplary arrangements discussed with respect to FIGS. 4A and 4B may be implemented in medical imaging systems based on the system 10 shown in FIG. 1, according to an embodiment of the present invention. FIGS. 5 and 6 each illustrate systems for generating composite real-time dynamic video streams using medical modalities comprising ultrasonography and endoscopy. Accordingly, FIGS. 5 and 6 comprise additional components and detail than which are shown in system 10 to discuss the present invention with respect to ultrasonography and endoscopy. However, it should be understood that the present invention is not limited to any particular modality, including any particular medical modality.

FIG. 5 is a schematic diagram illustrating a system 10' comprising an endoscope 42 and an ultrasound transducer 44 combined in a compound minimally-invasive instrument 48, according to an embodiment of the present invention. FIG. 5 is provided to illustrate an exemplary system in which the direct computation of the spatial relationship between the first video source 20 and the second video source 22 may be used. The compound minimally-invasive instrument 48 may be used to provide images of the scene based on multiple medical modalities using a single minimally-invasive instrument.

The compound minimally-invasive instrument 48 may penetrate into the body 46 of the subject, for example the patient, to align with the structure 24 and the region of interest 26 within the structure 24. In this embodiment, the structure 24 may be an organ within the body 46, and the region of interest 26 may be a growth or lesion within the structure 24. A surgeon may use the compound minimally-invasive instrument 48 to provide both an endoscopic and ultrasonogramic composite view to accurately target the region of interest 26 for any particular treatment and/or procedure.

The endoscope 42 may be connected, either optically or in some other communicable manner to a first video camera 50. Accordingly, the first video source 20 may be understood to comprise the endoscope 42 and the first video camera 50. The first video camera 50 may capture an image of the structure 24 through the endoscope 42. From the image captured by the first video camera 50, the first video camera 50 may produce a first real-time dynamic video stream of the image and send the first real-time dynamic video stream to the controller 12.

The ultrasound transducer 44 may be communicably connected to a second video camera 52. Accordingly, the second video source 22 may be understood to comprise the ultrasound transducer 44 and the second video camera 52. The ultrasound transducer 44 may detect an image of the region of interest 26 within the structure 24 and communicate the image detected to the second video camera 52. The second video camera 52 may produce a second real-time dynamic video stream representing the image detected by the ultrasound transducer 44, and then send the second real-time dynamic video stream to the controller 12.

Because the compound minimally-invasive instrument 48 comprises both the endoscope 42 and the ultrasound transducer 44, the first spatial state and the second spatial state may be fixed with respect to each other, and, accordingly, the spatial relationship of the first video source 20 and the second video source 22 may be determined by the direct computation discussed above with reference to FIG. 4A. This may be so even if the first video camera 50 and the second video camera 52, as shown in FIG. 5, are located remotely from the compound minimally-invasive instrument 48. In other words, the first video camera 50 and the second video camera 52 may not be included within the compound minimally-invasive instrument 48. As discussed above, the first spatial state and the second spatial state may be determined relative to a particular perspective of the image of the scene that is captured and/or detected. As such the first spatial state may be based on the position and displacement of the endoscope 42, while the second spatial state may be based on the displacement and position of the ultrasound transducer 44.

The first spatial state and the second spatial state may be received by the controller 12. The controller 12 may then determine the spatial relationship between the first video source 20, and the second video source 22 using the direct computation discussed above. Using the spatial relationship, the first real-time dynamic video stream and the second real-time dynamic video stream may be spatially registered to generate the composite representation 32. The composite real-time dynamic video stream may be generated from the composite representation 32. The controller 12 may then send the composite real-time dynamic video stream to the display 18.

FIG. 6 is a schematic diagram illustrating a system 10" comprising a separate endoscope 42 and an ultrasound transducer 44, according to an embodiment of the present invention; in this embodiment, the endoscope 42 comprises a laparoscope, and the ultrasound transducer 44 comprises a laparoscopic ultrasound transducer. FIG. 6 is provided to illustrate an exemplary system in which the direct computation of the spatial relationship between the first video source 20 and the second video source 22 may be used.

Accordingly, in FIG. 6, instead of one minimally-invasive instrument penetrating the body 46, two minimally-invasive instruments are used. The endoscope 42 may align with the structure 24. The ultrasound transducer 44 may extend further into the body 46 and may contact the structure 24 at a point proximal to the region of interest 26. In a similar manner to the system 10', the structure 24 may be an organ within the body 46, and the region of interest 26 may be a blood vessel, growth, or lesion within the structure 24. A surgeon may use the endoscope 42 and the ultrasound transducer 44 to provide a composite view of the structure 24 and the region of interest 26 to accurately target the region of interest 26 point on the structure 24 for any particular treatment and/or procedure.

To provide one of the images of the composite view for the surgeon, the endoscope 42 may be connected, either optically or in some other communicable manner, to a first video camera 50. Accordingly, the first video source 20 may be understood to comprise the endoscope 42 and the first video camera 50. The first video camera 50 may capture an image of the structure 24 through the endoscope 42. From the image captured by the first video camera 50, the first video camera 50 may produce a first real-time dynamic video stream of the image and send the first real-time dynamic video stream to the controller 12.

Additionally, to provide another image of the composite view for the surgeon, the ultrasound transducer 44 may be communicably connected to a second video camera 52. Accordingly, the second video source 22 may be understood to comprise the ultrasound transducer 44 and the second video camera 52. The ultrasound transducer 44 may detect an image of the region of interest 26 within the structure 24 and communicate the image detected to the second video camera 52. The second video camera 52 may produce a second real-time dynamic video stream representing the image detected by the ultrasound transducer 44 and then send the second real-time dynamic video stream to the controller 12.

Because the endoscope 42 and the ultrasound transducer 44 are separate, the first spatial state of the first video source 20 and the second spatial state of the second video source 22 may be determined using the indirect computation discussed above with reference to FIG. 4B. As discussed above, the indirect computation involves the use of an intermediary, such as a positional system. Accordingly, in system 10", an intermediary comprising a first transmitter 36, a second transmitter 38 and an infrared detection system 40 may be included. The first transmitter 36 may be located in association with the endoscope 42, and the second transmitter 38 may be located in association with the ultrasound transducer 44. Associating the first transmitter 36 with the endoscope 42 and the second transmitter 38 with the ultrasound transducer 44 may allow the first video camera 50 to be located remotely from the endoscope 42, and/or the second video camera 52 to be located remotely from the ultrasound transducer 44.

As discussed above with respect to the system 10', the first spatial state and the second spatial state may be determined with respect to the particular perspectives of the image of the scene that may be captured and/or detected by the first video source 20 and the second video source 22, respectively. As such the first spatial state may be based on the orientation and displacement of the endoscope 42, while the second spatial state may be based on the displacement and orientation of the ultrasound transducer 44. Additionally, in system 10' of FIG. 5, the endoscope 42 and the ultrasound transducer 44 are shown in a co-located arrangement in the compound minimally-invasive instrument 48. As such, the first spatial state of the first video source 20 and the second spatial state of the second video source 22 in addition to being fixed may also be very close relationally. Conversely, in the system 10", the orientation and displacement of the endoscope 42 and the ultrasound transducer 44 may be markedly different as shown in FIG. 6, which may result in the first spatial state of the first video source 20 and the second spatial state of the second video source 22 not being close relationally.

The infrared detection system 40 may determine the first spatial state of the first video source 20 and the second spatial state of the second video source 22 by detecting the light emitted from the first transmitter 36 and the second transmitter 38, respectively. The infrared detection system 40 may also determine the intermediary reference related to the position of the infrared detection system 40. The infrared detection system 40 may then send the first spatial state, the second spatial state, and the intermediary reference to the controller 12. The controller 12 may receive the first spatial state, the second spatial state, and the intermediary reference and may compute the spatial relationship between the first video source 20 and the second video source 22 using the indirect computation and, therefrom, the composite representation 32. As discussed above, the composite representation 32 represents the spatial registration of the first real-time dynamic video stream and the second real-time dynamic video stream. The controller 12 may then generate the composite real-time dynamic video stream from the composite representation 32.

For purposes of the present invention, the controller 12 may be understood to comprise devices, components and systems not shown in system 10' and system 10" in FIGS. 5 and 6. For example, the controller 12 may be understood to comprise an ultrasound scanner, which may be a Sonosite MicroMaxx, or similar scanner. Also, the controller 12 may comprise a video capture board, which may be a Foresight Imaging Accustream 170, or similar board. An exemplary video camera suitable for use in the system 10' and system 10" of FIGS. 5 and 6 is the Stryker 988 that has a digital IEEE 1394 output, although other digital and analog cameras may be used. The endoscope may be any single or dual optical path laparoscope, or similar endoscope.

Figures 7A, 7B, 7C:
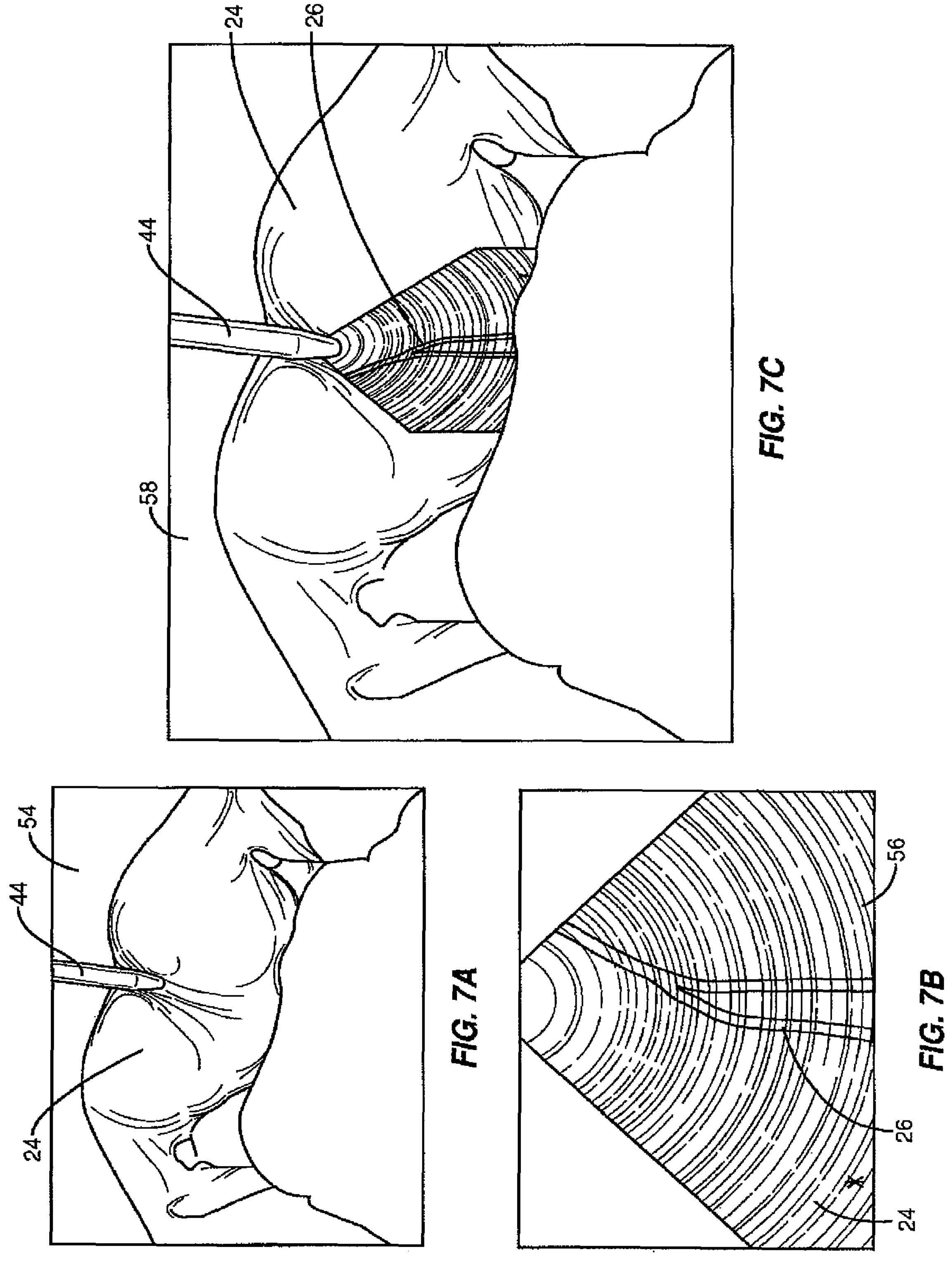
FIGS. 7A, 7B, and 7C are photographic representations of a frame from a laparoscopy-based real-time dynamic video stream, a frame of a two-dimensional medical ultrasonography-based real-time dynamic video stream, and a frame of a composite real-time dynamic video stream resulting from spatially registering the laparoscopy-based real-time dynamic video stream and the two-dimensional medical ultrasonography-based real-time dynamic video stream, according to an embodiment of the present invention.

FIGS. 7A, 7B, and 7C are photographic representations illustrating a first frame 54 from the first real-time dynamic video stream, a second frame 56 from the second real-time dynamic video stream, and a composite frame 58 of the composite real-time dynamic video stream generated from the spatial registration of the first real-time dynamic video stream and the second real-time dynamic video stream, according to an embodiment of the present invention. FIGS. 7A, 7B, and 7C are provided to further illustrate an embodiment of the present invention with reference to actual medical modalities, and the manner in which the composite real-time dynamic video stream based on multiple modalities may appear to a surgeon viewing a display.

In FIG. 7A, the first real-time dynamic video stream may be produced based on an endoscopic modality. In FIG. 7B, the second real-time dynamic video stream may be produced based on medical ultrasonographic modality. In FIG. 7A, the first real-time dynamic video stream shows the structure 24 in the form of an organ of the human body being contacted by an ultrasound transducer 44. FIG. 7B shows the second real-time dynamic video stream is produced using the ultrasound transducer 44 shown in FIG. 7A. In FIG. 7B the region of interest 26, which appears as blood vessels within the structure 24 is shown. In FIG. 7C, the composite real-time dynamic video stream generated shows the first real-time dynamic video stream and the second real-time dynamic video stream spatially registered. The second real-time dynamic video stream is merged with the first real-time dynamic video stream in appropriate alignment. As such the second real-time dynamic video stream is displaced and oriented in a manner as reflects the actual displacement and orientation of the region of interest 26 within the structure 24. In other words, the region of interest 26 is shown in the composite real-time dynamic video stream as it would appear if the surface of the structure 24 were cut away to make the region of interest 26 visible.

Figure 8:
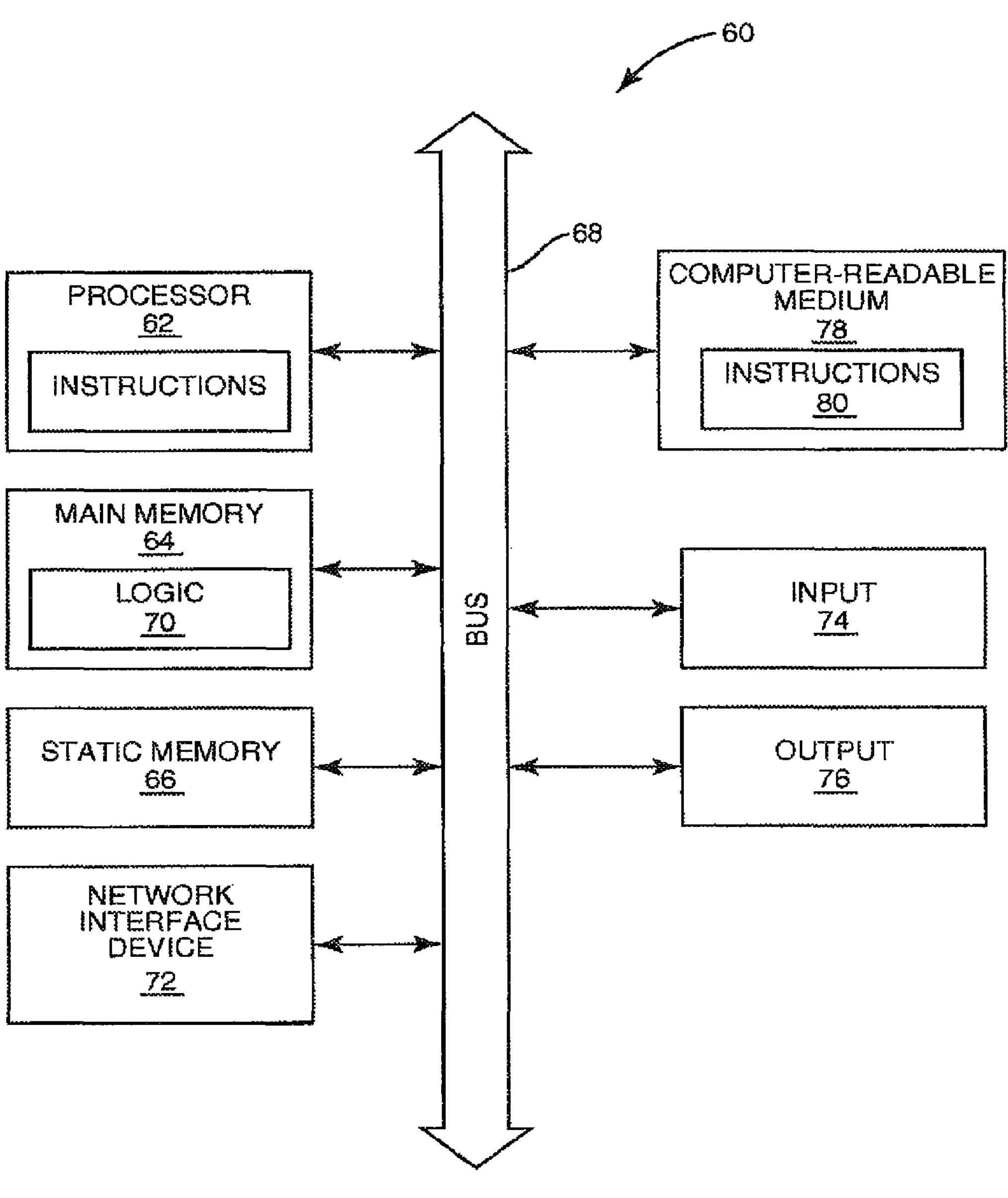
FIG. 8 illustrates a diagrammatic representation of a controller in the exemplary form of a computer system adapted to execute instructions from a computer-readable medium to perform the functions for spatially registering the first real-time dynamic video stream and the second real-time dynamic video stream for generating the composite real-time dynamic video stream according to an embodiment of the present invention.

FIG. 8 illustrates a diagrammatic representation of what a controller 12 adapted to execute functioning and/or processing described herein. In the exemplary form, the controller may comprise a computer system 60, within which is a set of instructions for causing the controller 12 to perform any one or more of the methodologies discussed herein. The controller may be connected (e.g., networked) to other controllers or devices in a local area network (LAN), an intranet, an extranet, or the internet. The controller 12 may operate in a client-server network environment, or as a peer controller in a peer-to-peer (or distributed) network environment. While only a single controller is illustrated, the controller 12 shall also be taken to include any collection of controllers and/or devices that individually or jointly execute a set (or multiple sets) of instructions to perform any one or more of the methodologies discussed herein. The controller 12 may be a server, a personal computer, a mobile device, or any other device.

The exemplary computer system 60 includes a processor 62, a main memory 64 (e.g., read-only memory (ROM), flash memory, dynamic random access memory (DRAM) such as synchronous DRAM (SDRAM) or Rambus DRAM (RDRAM), etc.), and a static memory 66 (e.g., flash memory, static random access memory (SRAM), etc.), which may communicate with each other via a bus 68. Alternatively, the processor 62 may be connected to the main memory 64 and/or the static memory 66 directly or via some other connectivity means.

The processor 62 represents one or more general-purpose processing devices such as a microprocessor, central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. The processor 62 is configured to execute processing logic 70 for performing the operations and steps discussed herein.

The computer system 60 may further include a network interface device 72. It also may include an input means 74 to receive input (e.g., the first real-time dynamic video stream, the second real-time dynamic video stream, the first spatial state, the second spatial state, and the intermediary reference) and selections to be communicated to the processor 62 when executing instructions. It also may include an output means 76, including but not limited to the display 18 (e.g., a head-mounted display, a liquid crystal display (LCD), or a cathode ray tube (CRT)), an alphanumeric input device (e.g., a keyboard), and/or a cursor control device (e.g., a mouse).

The computer system 60 may or may not include a data storage device having a computer-readable medium 78 on which is stored one or more sets of instructions 80 (e.g., software) embodying any one or more of the methodologies or functions described herein. The instructions 80 may also reside, completely or at least partially, within the main memory 64 and/or within the processor 62 during execution thereof by the computer system 60, the main memory 64, and the processor 62 also constituting computer-readable media. The instructions 80 may further be transmitted or received over a network via the network interface device 72.

While the computer-readable medium 78 is shown in an exemplary embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying a set of instructions for execution by the controller and that cause the controller to perform any one or more of the methodologies of the present invention. The term "computer-readable medium" shall accordingly be taken to include, but not be limited to, solid-state memories, optical and magnetic media, and carrier wave signals.

Those skilled in the art will recognize improvements and modifications to the preferred embodiments of the present invention. All such improvements and modifications are considered within the scope of the concepts disclosed herein and the claims that follow.

What is claimed is:

1. A method of providing real-time dynamic imagery of a medical procedure site, the method comprising:

receiving a first real-time dynamic video stream of a scene based on a first modality from a first medical device;

receiving a second real-time dynamic video stream of the scene based on a second modality from a second medical device;

obtaining at least one of first real-time spatial state data associated with the first medical device or second real-time spatial state data associated with the second medical device;

determining a relative orientation and position of the first medical device to the second medical device based on the at least one of the first real-time spatial state data or the second real-time spatial state data;

spatially registering the first real-time dynamic video stream and the second real-time dynamic video stream based on the determined relative orientation and position of the first medical device to the second medical device, wherein the first real-time dynamic video stream and the second real-time dynamic video stream align to form a composite representation of the scene; and generating a composite real-time dynamic video stream of the scene from the composite representation.

2. The method of claim 1, wherein the first modality comprises a two dimensional modality.

3. The method of claim 1, wherein the first modality comprises a three dimensional modality.

4. The method of claim 1, wherein the second modality comprises a two dimensional modality.

5. The method of claim 1, wherein the second modality comprises a three-dimensional modality.

6. The method of claim 1, wherein the first modality comprises endoscopy, and wherein the endoscopy comprises a modality selected from a group consisting of: laparoscopy, hysteroscopy, thoracoscopy, arthroscopy, colonoscopy, bronchoscopy, cystoscopy, proctosigmoidoscopy, esophagogastroduodenoscopy, and colposcopy.

7. The method of claim 1, wherein the second modality comprises a modality selected from a group consisting of: ultrasonography, magnetic resonance imaging, x-ray imaging, computed tomography, and optical wavefront imaging.

8. A system of providing real-time dynamic imagery of a medical procedure site, comprising:

a control system, wherein the control system is adapted to:

receive a first real-time dynamic video stream of a scene based on a first modality from a first medical device;

receive a second real-time dynamic video stream of the scene based on a second modality from a second medical device;

obtain at least one of first real-time spatial state data associated with the first medical device or second real-time spatial state data associated with the second medical device;

determine a relative orientation and position of the first medical device to the second medical device based on the at least one of the first real-time spatial state data or the second real-time spatial state data;

spatially register the first real-time dynamic video stream and the second real-time dynamic video stream based on the determined relative orientation and position of the first medical device to the second medical device, wherein the first real-time dynamic video stream and the second real-time dynamic video stream align to form a composite representation of the scene; and generate a composite real-time dynamic video stream of the scene from the composite representation.

9. A computer-readable non-transitory storage medium comprising computer-executable instructions that when executed by one or more processors, cause the one or more processors to:

receive a first real-time dynamic video stream of a scene based on a first modality from a first medical device;

receive a second real-time dynamic video stream of the scene based on a second modality from a second medical device;

obtain at least one of first real-time spatial state data associated with the first medical device or second real-time spatial state data associated with the second medical device;

determine a relative orientation and position of the first medical device to the second medical device based on the at least one of the first real-time spatial state data or the second real-time spatial state data;

spatially register the first real-time dynamic video stream and the second real-time dynamic video stream based on the determined relative orientation and position of the first medical device to the second medical device, wherein the first real-time dynamic video stream and the second real-time dynamic video stream align to form a composite representation of the scene; and generate a composite real-time dynamic video stream of the scene from the composite representation.

* * * * *